(12) United States Patent
Smith

(10) Patent No.: US 12,396,722 B2
(45) Date of Patent: *Aug. 26, 2025

(54) MOVABLE SUTURING APPARATUS AND METHOD

(71) Applicant: Gyrus ACMI, Inc., Westborough, MA (US)

(72) Inventor: Adam Lee Smith, Palm Desert, CA (US)

(73) Assignee: Gyrus ACMI, Inc., Westborough, MA (US)

( * ) Notice: Subject to any disclaimer, the term of this patent is extended or adjusted under 35 U.S.C. 154(b) by 89 days.

This patent is subject to a terminal disclaimer.

(21) Appl. No.: 17/215,660

(22) Filed: Mar. 29, 2021

(65) Prior Publication Data

US 2021/0298735 A1 Sep. 30, 2021

Related U.S. Application Data

(60) Provisional application No. 63/002,928, filed on Mar. 31, 2020, provisional application No. 63/002,995, filed on Mar. 31, 2020.

(51) Int. Cl.
*A61B 17/06* (2006.01)
*A61B 17/00* (2006.01)
(Continued)

(52) U.S. Cl.
CPC ........ *A61B 17/06066* (2013.01); *A61B 17/04* (2013.01); *A61B 17/0482* (2013.01);
(Continued)

(58) Field of Classification Search
CPC .............. A61B 17/06066; A61B 17/04; A61B 17/0482; A61B 17/06128; A61B 17/0625;
(Continued)

(56) References Cited

U.S. PATENT DOCUMENTS 5,545,148 A * 8/1996 Wurster ............. A61B 17/0469
606/147
6,015,416 A 1/2000 Stefanchik et al.
(Continued)

FOREIGN PATENT DOCUMENTS

CN 101505666 A 8/2009
CN 113456138 A 10/2021
(Continued)

OTHER PUBLICATIONS

Sep. 10, 2021, International Search Report for Application No. GB2104561.2.
(Continued)

*Primary Examiner* — Jocelin C Tanner
(74) *Attorney, Agent, or Firm* — Schwegman Lundberg & Woessner, P.A.

(57) ABSTRACT

Disclosed embodiments include apparatuses, systems, and methods for suturing a wound, incision, or other opening. In an illustrative embodiment, an apparatus includes a helically-shaped needle having a helical radius, the needle having a shaft and drawing a filament from a trailing end. Two generally-parallel rollers are configured to engage therebetween the shaft, the first roller having a roller radius that is less than the helical radius of the needle to enable the needle to revolve around the first roller to pierce a body adjacent the first roller and to draw the filament therethrough. A frame is configured to counter-rotatably support the rollers. The frame includes couplings configured to detachably receive distal ends of a support shaft and drive member extending from a drive mechanism, the drive member being configured to provide the rotational force to at least one of the rollers.

23 Claims, 20 Drawing Sheets

(51) Int. Cl.
*A61B 17/04* (2006.01)
*A61B 17/062* (2006.01)
*A61B 34/30* (2016.01)

(52) U.S. Cl.
CPC .... *A61B 17/06128* (2013.01); *A61B 17/0625* (2013.01); *A61B 34/30* (2016.02); *A61B 2017/00398* (2013.01); *A61B 2017/00473* (2013.01); *A61B 2017/0498* (2013.01); *A61B 2017/06076* (2013.01)

(58) Field of Classification Search
CPC .......... A61B 34/30; A61B 2017/00398; A61B 2017/00473; A61B 2017/0498; A61B 2017/06076; A61B 2017/00876; A61B 2017/047; A61B 17/0491; A61B 17/11
USPC ........................................................ 606/144
See application file for complete search history.

(56) References Cited

U.S. PATENT DOCUMENTS

| | | | |
|---|---|---|---|
| 6,613,058 | B1 | 9/2003 | Goldin |
| 9,962,155 | B2 | 5/2018 | Meade et al. |
| 10,736,625 | B1 | 8/2020 | Penn, IV et al. |
| 2006/0212048 | A1* | 9/2006 | Crainich ............ A61B 17/0469 606/144 |
| 2015/0127024 | A1 | 5/2015 | Berry |
| 2019/0290259 | A1* | 9/2019 | Sikes ............... A61B 17/06123 |
| 2019/0343529 | A1 | 11/2019 | Smith et al. |
| 2019/0388087 | A1 | 12/2019 | Almodovar |
| 2020/0375591 | A1* | 12/2020 | Mohamed .......... A61B 17/0482 |
| 2021/0298749 | A1 | 9/2021 | Smith |
| 2022/0061836 | A1* | 3/2022 | Parihar ................ A61B 17/072 |

FOREIGN PATENT DOCUMENTS

| | | |
|---|---|---|
| DE | 102021107650 A1 | 9/2021 |
| FR | 3108491 A1 | 10/2021 |
| GB | 2590138 A | 6/2021 |
| GB | 2595352 A | 11/2021 |
| GB | 2595352 B | 10/2024 |
| JP | 2013529982 A | 7/2013 |
| JP | 2021159773 A | 10/2021 |
| JP | 7555872 B2 | 9/2024 |
| WO | WO-2004066848 A1 | 8/2004 |
| WO | WO-2019246437 A1 | 12/2019 |

OTHER PUBLICATIONS

"U.S. Appl. No. 17/215,528, Non Final Office Action mailed Aug. 8, 2022", 16 pgs.
"U.S. Appl. No. 17/215,528, Response filed Nov. 1, 2022 to Non Final Office Action mailed Aug. 8, 2022", 13 pgs.
"French Application Serial No. 2103364, Office Action mailed Jul. 28, 2022", with machine translation, 6 pgs.
"French Application Serial No. 2103364, Response filed Oct. 7, 2022 to Office Action mailed Jul. 28, 2022", with English claims, 10 pgs.
"U.S. Appl. No. 17/215,528, Final Office Action mailed Mar. 22, 2023", 18 pgs.
"U.S. Appl. No. 17/215,528, Non Final Office Action mailed Jul. 28, 2023", 19 pgs.
"U.S. Appl. No. 17/215,528, Response filed May 22, 2023 to Final Office Action mailed Mar. 22, 2023", 11 pgs.
"Japanese Application Serial No. 2021-057296, Notification of Reasons for Refusal mailed Mar. 20, 2023", w/ English Translation, 14 pgs.
"Japanese Application Serial No. 2021-057296, Response filed Jun. 20, 2023 to Notification of Reasons for Refusal mailed Mar. 20, 2023", w/ english claims.
"U.S. Appl. No. 17/215,528, Appeal Brief filed May 29, 2024", 24 pgs.
"U.S. Appl. No. 17/215,528, Decision on Pre-Appeal Brief mailed Apr. 30, 2024", 2 pgs.
"U.S. Appl. No. 17/215,528, Final Office Action mailed Jan. 26, 2024", 22 pgs.
"U.S. Appl. No. 17/215,528, Pre-Appeal Brief Request for Review filed Mar. 26, 2024", 5 pgs.
"Chinese Application Serial No. 202110341879.6, Office Action mailed Jul. 9, 2024", w/ English Translation, 23 pgs.
"French Application Serial No. 2103364, Response filed Jan. 4, 2024 to Office Action mailed Oct. 5, 2023", w/o claims, 21 pgs.
"Japanese Application Serial No. 2021-057296, Examiners Decision of Final Refusal mailed Mar. 18, 2024", w/ English translation, 6 pgs.
"Japanese Application Serial No. 2021-057296, Response filed Jul. 18, 2024 to Examiners Decision of Final Refusal mailed Mar. 18, 2024", w/ current English claims, 12 pgs.
"Japanese Application Serial No. 2021-057296, Response filed Dec. 19, 2023 to Notification of Reasons for Rejection mailed Sep. 19, 2023", w/ english claims, 12 pgs.
"United Kingdom Application Serial No. 2104561.2, First Examination Report mailed Apr. 2, 2024", 2 pgs.
"United Kingdom Application Serial No. 2104561.2, Response filed Jun. 3, 2024 to First Examination Report mailed Apr. 2, 2024", w/ claims, 14 pgs.
"United Kingdom Application Serial No. 2104561.2, Subsequent Examination Report under Section 18 (3) mailed Jun. 18, 2024", 3 pgs.
"Chinese Application Serial No. 202110341879.6, Response filed Oct. 18, 2024 to Office Action mailed Jul. 9, 2024", w/ english claims, 14 pgs.
"United Kingdom Application Serial No. 2104561.2, Response filed Aug. 12, 2024 to Subsequent Examination Report under Section 18 (3) mailed Jun. 18, 2024", 8 pgs.
"United Kingdom Application Serial No. 2413777.0, Office Action mailed Nov. 14, 2024", 2 pgs.
"U.S. Appl. No. 17/215,528, Response filed Oct. 30, 2023 to Non Final Office Action mailed Jul. 28, 2023", 11 pgs.
"French Application Serial No. 2103364, Office Action mailed Oct. 5, 2023", w/o English Translation, 1 pg.
"Japanese Application Serial No. 2021-057296, Notification of Reasons for Rejection mailed Sep. 19, 2023", w/ English Translation, 8 pgs.

* cited by examiner

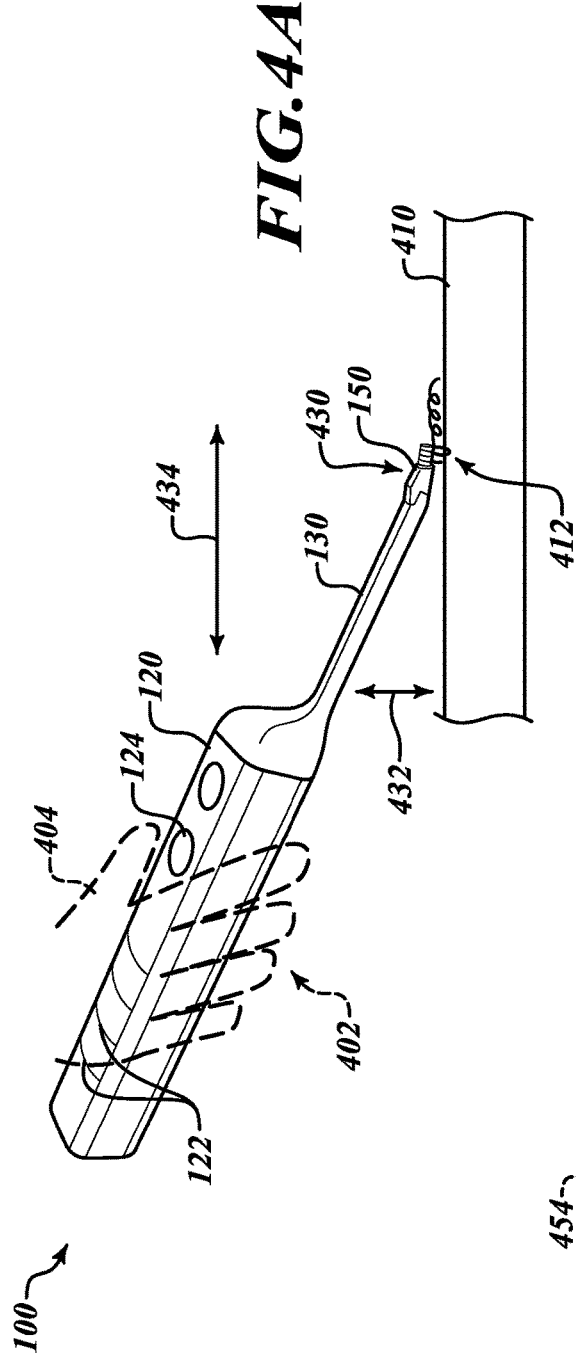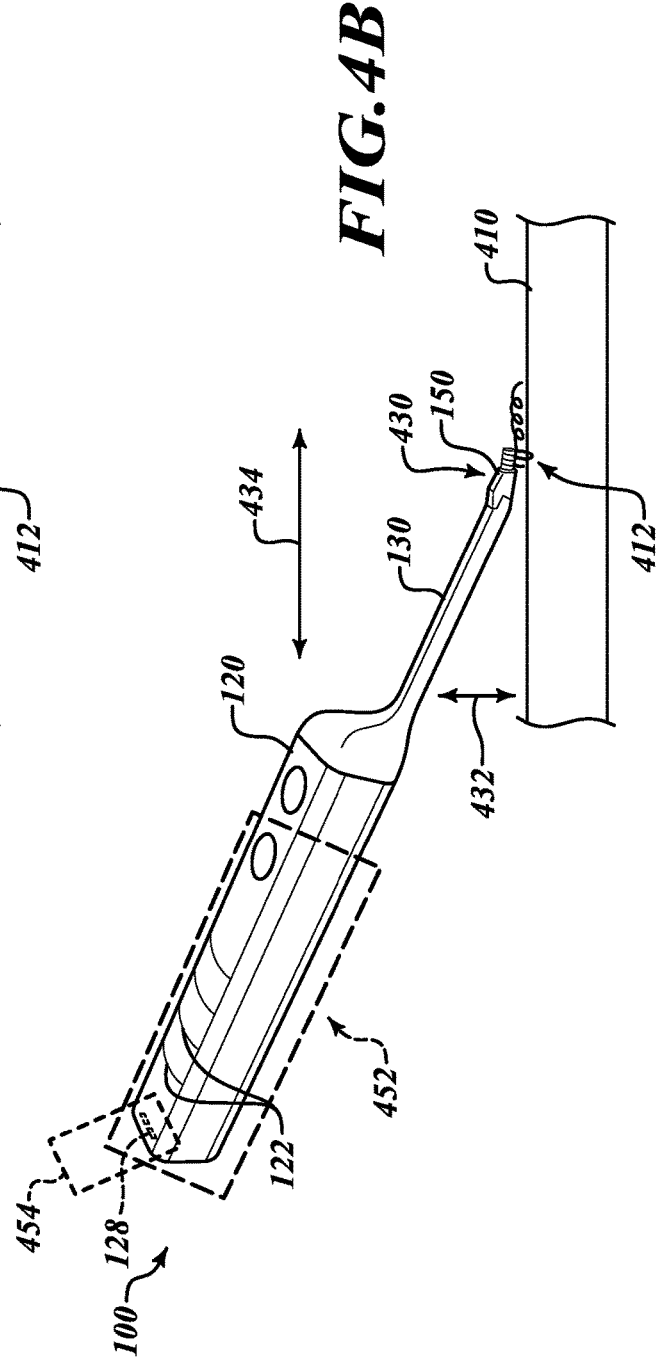

MOVABLE SUTURING APPARATUS AND METHOD

PRIORITY CLAIM

The present application claims the priority and benefit of U.S. Provisional Patent Application Ser. No. 63/002,928 and U.S. Provisional Patent Application Ser. No. 63/002,995, both filed Mar. 31, 2020 and entitled "MOVABLE SUTURING APPARATUS AND METHOD."

FIELD

The present disclosure relates to apparatuses, systems, and methods for suturing an object.

BACKGROUND

The statements in this section merely provide background information related to the present disclosure and may not constitute prior art.

Sutures are commonly used to close incisions or wounds. Sutures typically are formed by passing a curved needle through tissue at both sides of the incision or wound, with the needle drawing a filament from a trailing end. Once the curved needle completes a full revolution around the incision or wound, the filament forms a suture to hold the tissue closed.

Although the process itself is well known, the process of positioning the needle at a desired location and motivating the needle may not be simple. It may be difficult for a person suturing a wound or incision to reach the location and motivate the needle through the tissues, even when the suturing is performed by a skilled and/or experienced medical provider.

SUMMARY

Disclosed embodiments include apparatuses, systems, and methods for suturing a wound, incision, or other opening.

In an illustrative embodiment, an apparatus includes a roller mechanism configured to counter-rotatably support two generally-parallel rollers configured to engage therebetween a shaft of a helically-shaped needle, the needle having a point at a leading end, drawing a filament from a trailing end, and having a first helical radius, the needle being revolvable around a first roller having a roller radius that is less than a helical radius of the needle to enable the needle to pierce a body and draw a filament through a body disposed adjacent the first roller. A motor drive is operably coupled with roller mechanism to convey rotational force to rotate the two generally-parallel rollers. A controller is operably coupled with the motor drive and configured to cause the needle to complete at least one revolution to form a single suture in the body.

In another embodiment, a system includes a helically-shaped needle having a helical radius, the needle having a point at a first end of a shaft and a filament joined to a second end. A roller mechanism is configured to counter-rotatably support two generally-parallel rollers configured to engage therebetween the shaft of the needle, the needle being revolvable around a first roller having a roller radius that is less than a helical radius of the needle to enable the first end of the needle to pierce a body and draw the filament through a body disposed adjacent the first roller. A motor drive includes a motor operably coupled with the roller mechanism to convey rotational force to rotate the two generally-parallel rollers and a controller operably coupled with the motor and configured to cause the needle to complete at least one revolution to form a single suture in the body.

In a further embodiment, in an illustrative method, positioning a first roller of two generally-parallel rollers is positioned adjacent to a body, wherein the two generally-parallel rollers engage therebetween a helically-shaped needle, where the needle draws a filament from a trailing end, has a first helical radius that is greater than a radius of the first roller, and is revolvable around the first roller to enable the needle to pierce and extend through a body. An input is provided to a motor operably coupled with at least one of the two generally-parallel rollers, wherein the input causes the motor to rotate so as to cause the two-generally parallel rollers to rotate so as to cause the needle to complete at least one revolution to form a single suture.

In an additional illustrative embodiment, an apparatus includes a helically-shaped needle having a first helical radius, the needle having a shaft and drawing a filament from a trailing end. Two generally-parallel rollers are configured to engage therebetween the shaft of the needle, the first roller having a roller radius that is less than the helical radius of the needle to enable the needle to revolve around the first roller to pierce a body disposed adjacent the first roller and to draw the filament through the body. A frame is configured to counter-rotatably support the rollers. The frame includes a support coupling configured to detachably receive a distal end of a support shaft extending from a drive mechanism and a drive coupling configured to detachably receive a distal end of a drive member extending from the drive mechanism, the drive member being configured to provide the rotational force to at least one of the rollers.

In another illustrative embodiment, a drive mechanism includes a housing, a motor supported by the housing, a support shaft extending from the housing, and a drive member coupled with the motor and supported by the shaft where the drive member is configured to convey rotational force from the motor. A suture cartridge includes a helically-shaped needle having a first helical radius, the needle having a shaft and drawing a filament from a trailing end. Two generally-parallel rollers are configured to engage therebetween the shaft of the needle, the first roller having a roller radius that is less than the helical radius of the needle to enable the needle to revolve around the first roller to pierce a body disposed adjacent the first roller and to draw the filament through the body. A frame is configured to counter-rotatably support the rollers. The frame includes a support coupling configured to detachably receive a distal end of the support shaft and a drive coupling configured to detachably receive a distal end of the drive member and to convey the rotational force to at least one of the rollers.

In still another embodiment, an illustrative method includes engaging a suture cartridge with a motor drive. The suture cartridge supports a pair of generally-parallel rollers rotatably engaging a shaft of a helically-shaped needle therebetween, the needle being rotatable around a first roller and having a helical radius greater than that of a roller radius of the first roller to enable the needle to pierce and extend through a body disposed adjacent the first roller. The first roller of two generally-parallel rollers is positioned adjacent to the body. An input is provided to the motor drive, wherein the input causes the motor drive to rotate the two-generally parallel rollers to rotate so as to cause the needle to complete at least one revolution to form a single suture.

Further features, advantages, and areas of applicability will become apparent from the description provided herein.

It will be appreciated that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings:

FIGS. 4A and 4B are perspective views of the apparatus of FIG. 1 positioned to suture an object by a human hand and a robotic actuator, respectively;

DETAILED DESCRIPTION

The following description explains, by way of illustration only and not of limitation, various embodiments of apparatuses, systems, and methods for suturing an opening in a body, such as a wound or an incision. It will be noted that the first digit of three-digit reference numbers and the first two digits of four-digit reference numbers correspond to the figure number in which the element first appears.

By way of a non-limiting introduction and overview, an apparatus and system of the present disclosure employ a motor drive to motivate two generally-parallel rollers that engage opposing faces of a shaft of a helical needle. A first of the two rollers is disposed adjacent to an opening in a body, such as a wound or an incision. The helical needle and the first roller have radii that are sized to enable the helical needle to revolve around the first roller and through tissues on opposing sides of the opening. A trailing end of the helical needle draws a filament. When the motor drive causes the rollers to revolve the needle through a full revolution, a suture is formed to close the opening. In various embodiments, the motor drive has a controller that, upon the pressing of a button or receipt of another discrete input, causes a motor to form a single suture. Thus, by positioning the rollers and the needle at the location where the suture is desired and providing a single input, a suture may be formed without an operator or actuator having to be moved to manually draw the needle through the body to form the suture.

In various embodiments, the motor drive may be detachably engaged to a suture cartridge that supports the rollers and the needle. As a result, different cartridges may be detachably and disposably engaged by a motor drive to form sutures on different parts of a body or on different bodies. The motor drive may be reused, while suture cartridge including the rollers and needle may be discarded. Further, alternative suture cartridges may support differently-sized needles to support formation of differently-sized sutures for different applications.

Now that an overview has been given, details of various embodiments will be explained by way of non-limiting examples given by way of illustration only and not of limitation.

Figure 1:
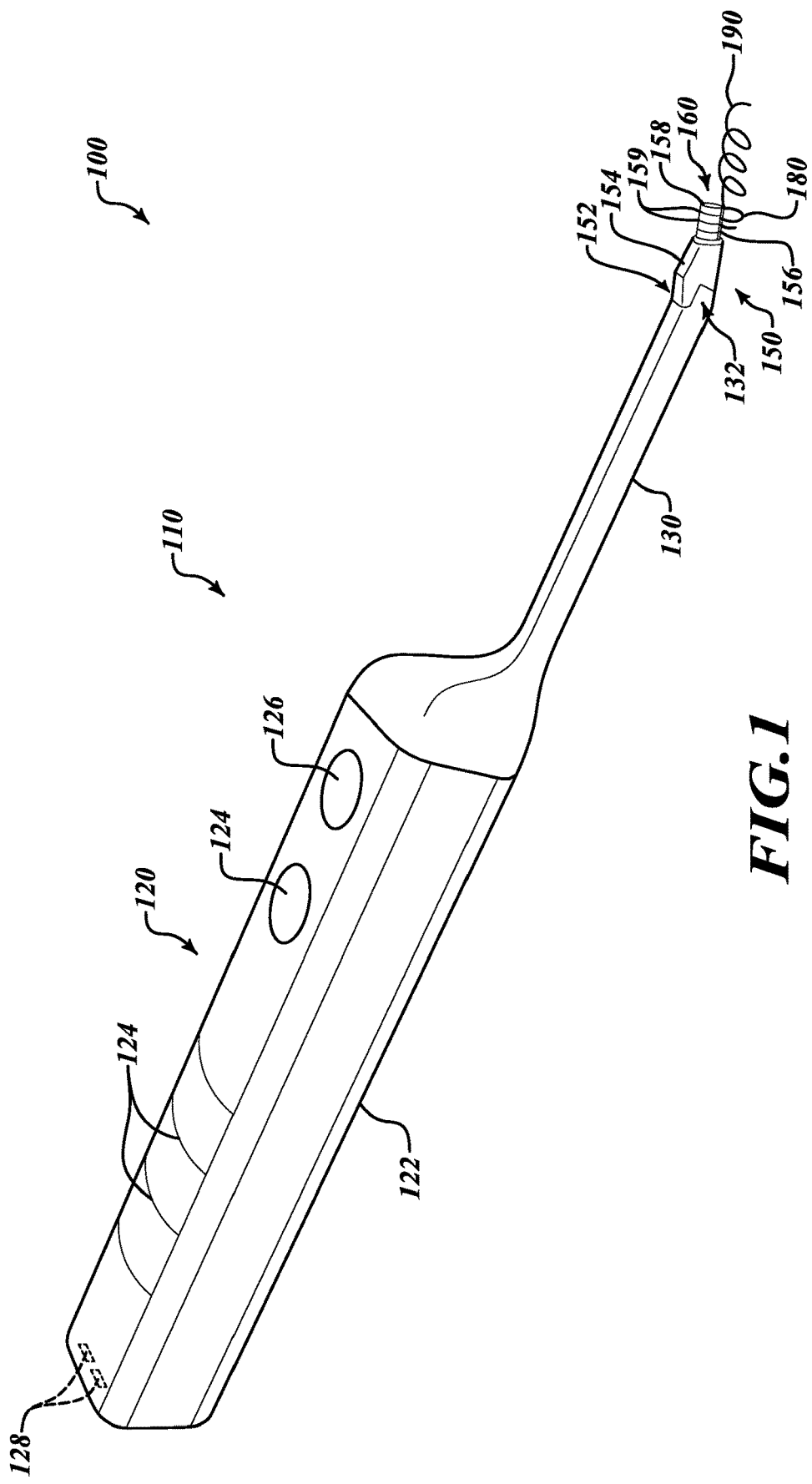
FIG. 1 is a perspective view of an embodiment of an apparatus for suturing an object.

Referring additionally to FIG. 1, in an apparatus 100 includes a motor drive 120 coupled with a roller mechanism 150 that motivates a helical needle 180 that draws a filament 190 to form a suture (not shown in FIG. 1). The motor drive 120 includes a housing 122 that supports and/or contains other components of the motor drive 120. The housing 122 includes an interface (e.g., suture control 124, also referenced as control 124) that facilitates the housing 122 being gripped by a human operator or supported by a robotic arm or other mechanical actuator (not shown in FIG. 1). The interface (e.g. suture control 124) may be shaped or textured to aid in the operator or actuator being able to securely hold the housing 122.

The housing 122 may support one or more controls 124 and 126 that control operation of the motor drive 120. In various embodiments, and as further described below, a suture control 124 may cause components of the motor drive 120 to revolve the needle 180 through one revolution to form a single suture. A second control 126 may be configured to stop and/or reverse the revolution of the needle 180 as desired. Electrical inputs 128 may be included to allow provision of power from an external source (not shown) to the motor and other components (not shown in FIG. 1). The electrical inputs 128 also may be used to provide input signals instead of or in addition to the controls 124 and 126. For example, the use of such inputs 128 may allow a human operator to trigger the formation of a suture by activating a foot pedal (not shown) or other external control. In addition, if the apparatus 100 is employed by a robotic arm or other actuator, the inputs 128 may allow the actuator to control the apparatus 100 without having to physically engage the controls 124 and 126.

In various embodiments, a shaft 130 extends from the housing 122 to support the roller mechanism 150. The shaft 130 may be sized and shaped to allow the roller mechanism 150 to be conveniently positioned away from the housing 122 to form sutures without the housing 122 and/or the operator's hand or other supporting body having to be placed close to the opening to be sutured. Distancing the housing 122 from the roller mechanism 150 thus may afford the operator greater visibility of the opening to be sutured and provide additional freedom of movement than if the housing 122 had to be positioned immediately adjacent the opening to be sutured. The shaft 130 may mechanically support the roller mechanism 150 and house a drive member (not shown in FIG. 1) that provides rotational force to the roller mechanism 150, as further described below.

Figure 2:
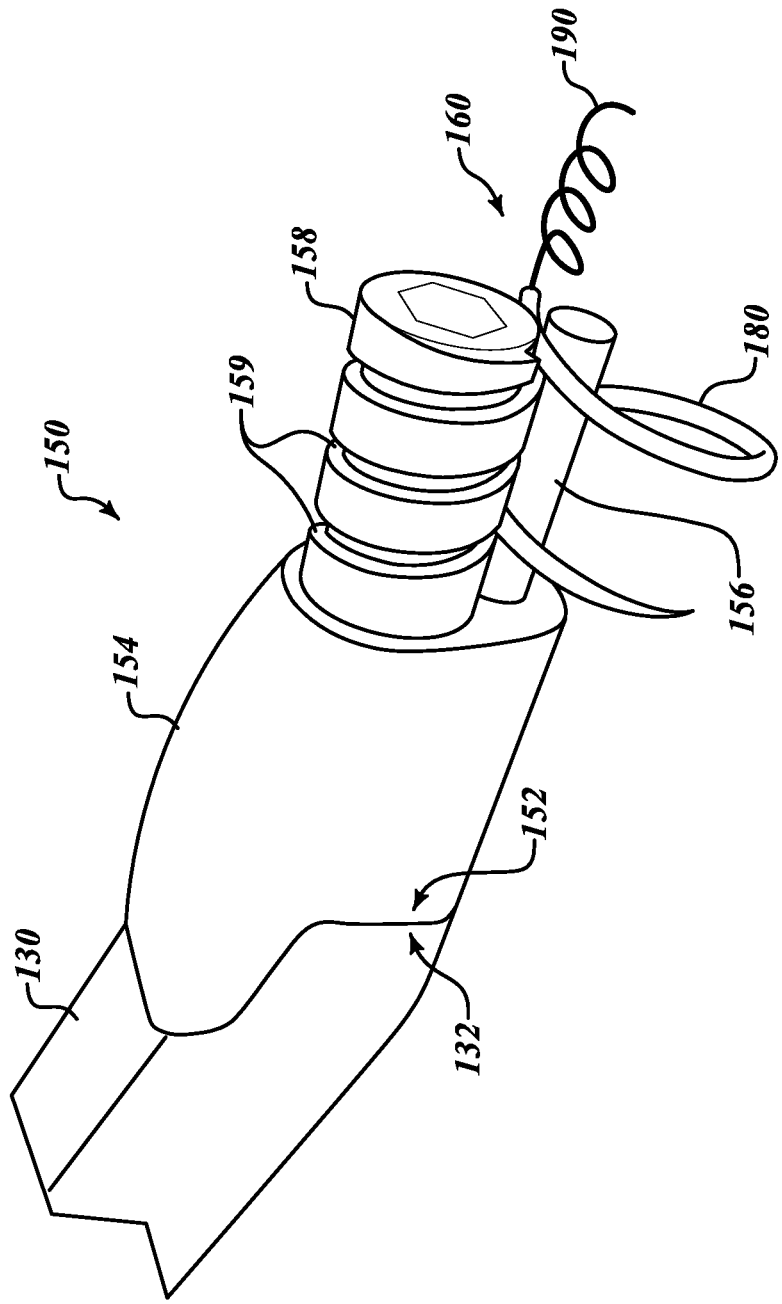
FIG. 2 is a perspective view of a roller mechanism of the apparatus of FIG. 1.

Referring additionally to FIG. 2, the roller mechanism 150 may include a frame 154 that supports the rollers 156 and 158 that motivate the needle 180 which, in turn, draws the filament 190 that forms the suture. The frame 154, as further described below, may be detachably coupled with the shaft 130. A proximal end 152 of the frame 150 may engage a distal end 132 of the shaft 130. The previously-mentioned drive coupling (not shown) may extend across and/or through the junction of the distal end 132 of the shaft 130 and the proximal end 152 of the frame to provide rotational force to the rollers 156 and 158.

The first roller 156 may be positioned adjacent to the opening in the body (not shown in FIGS. 1 and 2) to be sutured with the helical needle 180 being positioned to orbit around the first roller 156 to pierce the body and draw the filament 190 therethrough. A shaft of the needle 180 is engaged on opposing sides by the first roller 156 and the second roller, and the rollers 156 and 158 are counter-rotated to cause the needle 180 to revolve eccentrically around the first roller 156. As further described below, the second roller 158 may include grooves 159 to partially receive the needle 180 to positionally secure the needle 180 as it is revolved to form a suture. An open end 160 of the frame 150 enables the filament 190 to be drawn by the needle 180 without the filament 190 having to be directed around or potentially being obstructed by a frame at the open end 160.

Figure 3:
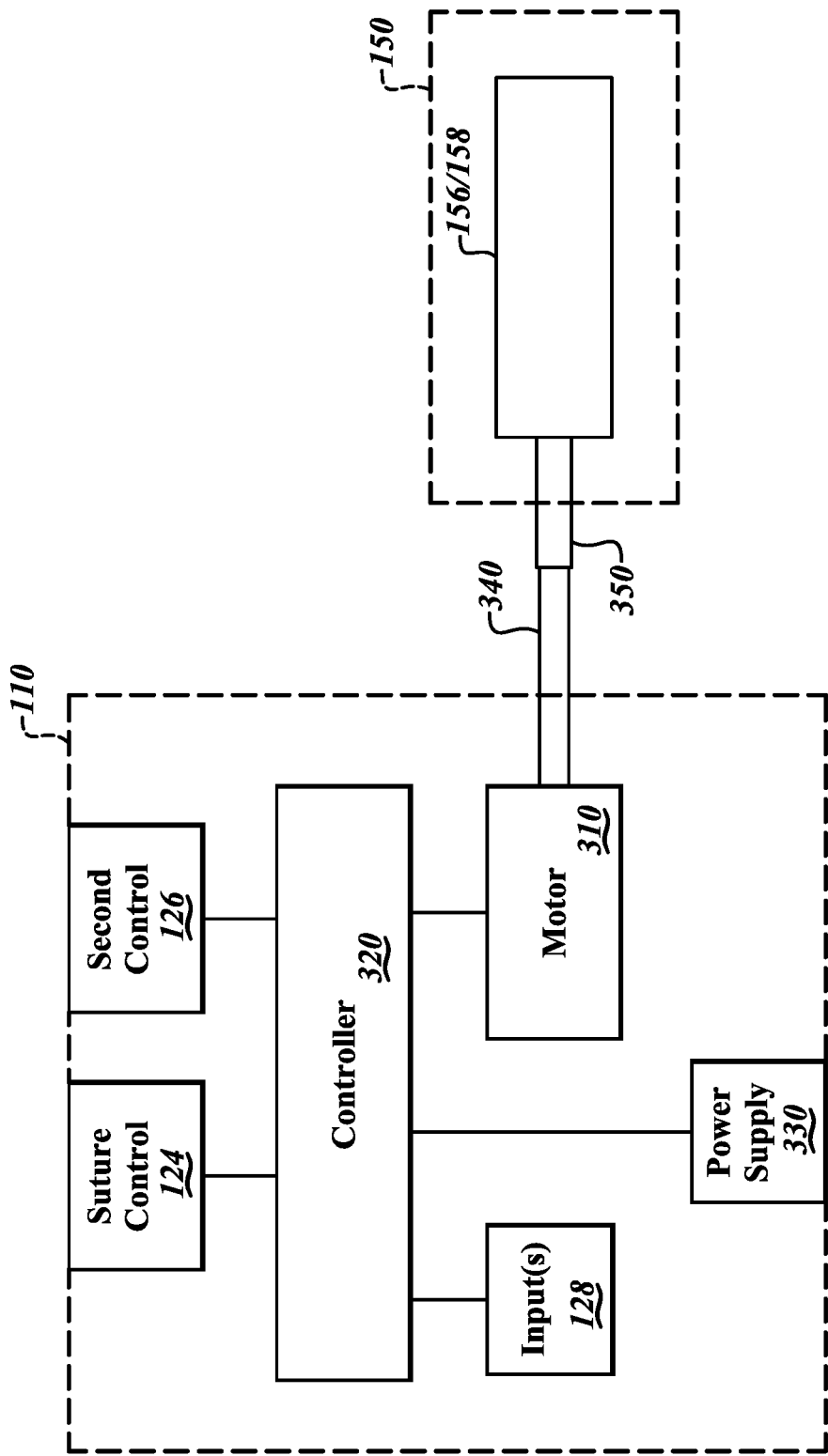
FIG. 3 is a schematic block diagram of components of the apparatus of FIG. 1.

Referring additionally to FIG. 3, in various embodiments the motor drive 110 includes components that support the functions previously described. As previously described, the motor drive 110 includes the suture control 124, the second control 126, and the electrical inputs 128. In such embodiments the motor drive 110 also may include a motor 310, a controller 320, a power supply 330, and a drive member 340.

In various embodiments, the motor 310 is any type of electrical motor that provides a selectively-activated source of rotational force that is transmitted to the roller mechanism 150. The motor 310 is mechanically coupled to a drive member 340, such as a drive shaft or drive cable. As further described below, the drive member 340 is operably couplable with a drive coupling 350 of the roller mechanism 150. The drive member 340, which may be a drive shaft or drive cable that is mechanically coupled with at least one of the rollers 156 or 158, receives the rotational force from the motor 310 via the drive member 340 and the drive coupling 350 to rotate at least one of the rollers 156 and 158 to motivate the needle 180 to form sutures, as further described below.

In various embodiments the motor 310 is coupled with the controller 320 which, in various embodiments, is coupled with the suture control 124, the second control 126, the electrical inputs 128, and a power supply 330. In various embodiments, the controller 320 is a logic circuit or microprocessor configurable, upon receipt of a control input received from the suture control 124, the second control 126, and/or the electrical inputs 128, directs operation of the motor 310. As previously described, when a user engages the suture control 124 (or a similar instruction is received via the electrical inputs 128), the controller 320 causes the motor 310 to rotate to cause the roller mechanism 150 to revolve the needle 180 (FIGS. 1 and 2) to complete a revolution to form a suture. The controller 320 receives power from the power supply 330 contained within the motor drive 110 or from an external power supply via the electrical inputs 128 and selectively provides electrical power to the motor 310 to cause the motor 310 to provide generate rotational force. As also previously described, when a user engages the second control 126 (or a similar instruction is received via the electrical inputs 128), the controller 320 causes the motor 310 to stop or reverse, when desired.

Referring additionally to FIGS. 4A and 4B, the apparatus 100 may be shaped to facilitate ease of operation. In various embodiments, the shaft 130 may include an angled portion 430 to enable the housing 122 to be positioned at a first displacement 432 from a body 410 to be sutured while the roller mechanism 150 is disposed at a location 412 where the suture is to be placed. The angled portion 430 allows for the first displacement 432 provides space for a hand of a human operator 404 (FIG. 4A) or an actuator of an electromechanical device 452 (FIG. 4B) supporting the apparatus 100 to hold the apparatus 100 in place without abutting the body 410.

Similarly, the shaft 130 may be configured to permit a second displacement 434 between the housing 120 and the roller mechanism 150 so that the motor drive 120 does not need to be placed immediately adjacent the location 412. Allowing for the second displacement 434 may permit the roller mechanism 150 to be inserted at a location where the motor drive 120 may not fit because of other structures (not shown) or so as not to prevent the motor drive 120 from blocking a view of the location 412.

Referring again to FIG. 4A, it will be appreciated that, with a user's hand 402 supporting the apparatus 100, the user may hold the apparatus 100 with one hand at the location 412 and may initiate formation of a suture by engaging the suture control 124 with a human operator 404 (via a thumb or other finger, depending on placement of the suture control 124 and the hand). Referring again to FIG. 4B, with the actuator 452 supporting the apparatus 100, the actuator 452 may position the apparatus at the location 412 and may initiate formation of a suture by sending a control signal to the electrical input 128 via a signal coupling 454. In either case, a suture may be formed at the location 412 without the effort or the space required for a person to use one or both of his hands at the location 412 to push and pull a needle through the body to form a suture.

Figure 5:
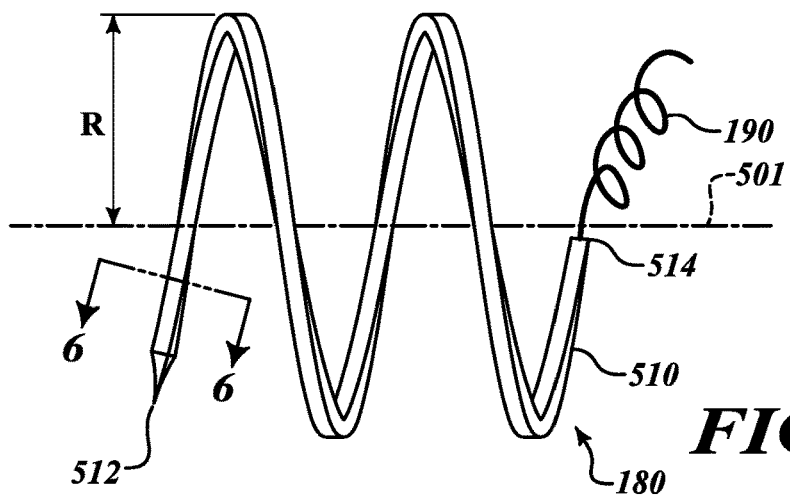
FIG. 5 is a side view of a helical needle usable with the apparatus of FIG. 1.

Referring additionally to FIG. 5, the helical needle 180 has an axis 501 about which it revolves when motivated by the counter-rotating rollers 156 and 158 (FIGS. 1 and 2). As shown below in FIGS. 1 and 2, the axis 501 is not positioned coaxially with axes of either of the rollers 156 and 158. Instead, the axis 501 is parallel with the axes of the rollers 156 and 158, thereby enabling the needle 180 to be revolved by the rollers 156 and 158 while rotating about its own axis 501 and to engage the body 410 (FIGS. 4A and 4B) on a side of the needle 180 opposite the side of the needle 180 where it is engaged between the rollers 156 and 158. In various embodiments, a shaft 510 of the needle 180 may have a rectangular or square cross-section, as described further below. The needle 180 has a pointed leading end 512 and draws the filament 190 from a trailing end 514. In various embodiments, the filament 190 is coupled to the trailing end 514, such as by the trailing end 514 being crimped around an end of the filament 190.

Figure 6:
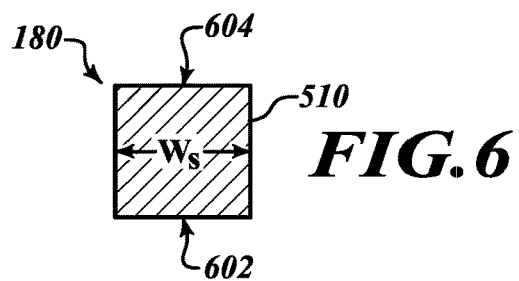
FIG. 6 is a cross-sectional view of the needle of FIG. 5.

Referring additionally to FIG. 6, in a section of the shaft 510 of the needle 180 taken along axis 6-6 of FIG. 5, the shaft 510 of the needle 180 has opposing flat surfaces 602 and 604 on opposing sides of a generally rectangular or square cross-section 600. The flat surfaces 602 and 604 have a width $w_s$. The opposing flat surfaces 602 and 604 are engageable on one side within the groove 159 of the roller 158 (FIGS. 1 and 2) and, on the other side, by a surface of the roller 156.

Figure 7:
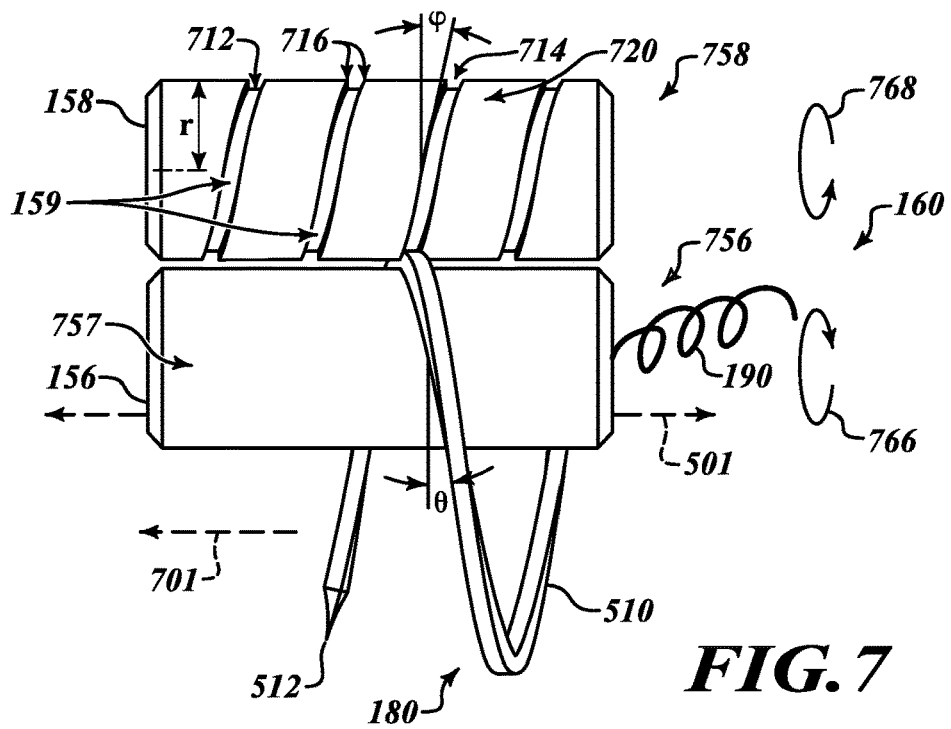
FIG. 7 is a side view of the needle of FIG. 5 engaged by rollers of the apparatus of FIGS. 1 and 2.

Referring additionally to FIG. 7, the shaft 510 of the needle 180 is received within the groove 159 of the roller 158. In various embodiments, the groove 159 has a rectangular cross-section. The groove 159 is bounded by a generally flat bottom 712 that is bounded by generally flat sides 716 that each extend to an opening 714 at a grooved surface 720 of the roller 158. The roller 156 has a flat surface 757. The shaft 510 of the needle 180 is thus engaged between the groove 159 of the roller 158 at one side and the flat surface 757 of the roller 156 on an opposite side. The rollers 156 and 158 have open distal ends 756 and 758 at the open end 160 of the apparatus 100 (FIGS. 1 and 2), respectively. The open distal ends 756 and 758 of the rollers 156 and 158, respectively, allow the filament 190 to be drawn by the trailing end 514 (not shown in FIG. 7) of the needle 180 without the filament 190 being routed through or around a distal mount or other similar obstruction.

The rollers 156 and 158 counter-rotate to revolve the needle 180, with the roller 156 rotating in a direction 766 and the roller 158 counter-rotating in an opposite direction 768. With the needle 180 disposed to revolve eccentrically about the roller 156, the needle 180 revolves in the same direction 756 as the roller 156. The rollers 156 and 158 may be mechanically interconnected, by gears or similar rotatable linkages (not shown in FIG. 7) to cause the rollers 156 and 158 to counter-rotate. Alternatively, because the rollers 156 and 158 are the frictionally engaged with opposite sides of the shaft 510 of the needle 180, rotation of one of the rollers 156 or 158 would cause the opposite roller to counter rotate. In various embodiments, the leading end 512 of the needle 180 is disposed to advance in a direction 701 away from the open end 160 of the apparatus 100 as the rollers 156 and 158 are counter-rotated.

Continuing to refer to FIG. 7, it will be appreciated that a pitch of the groove φ is ratiometrically-matched to a pitch of the needle θ according to a ratio of a helical radius R (FIG. 5) of the needle 180 to a radius r of the roller 158. As a result, the needle 180 will align with the groove 159 as the roller 158 is rotated along with the roller 156 in motivating the needle 180.

Figure 8:
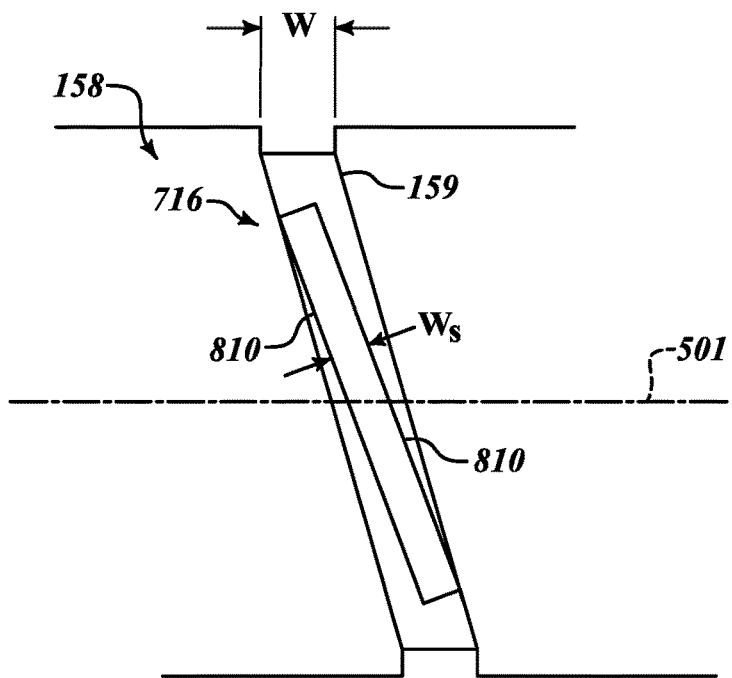
FIG. 8 is a top-down view of a portion of the needle of FIG. 5 received in a groove of one of the rollers of FIG. 7.

Referring additionally to FIG. 8, with the groove 159 of the roller 158 having a width W larger than the width $W_s$ of the shaft 512 of the needle 180 fits within the groove 159 without the sides 716 of the groove 159 impinging upon the sides 810 of the shaft 512 of the needle 180. As a result, the widened width W of the groove 159 avoids undesirable effects, such as compression of the needle 180 along its axis 501. In various embodiments, using a groove width W that is 20 percent larger than the width $W_s$ of the shaft 510 of the needle 180 suitably accommodates the shaft 510 of the needle 180 within the groove 159 without the sides 716 impinging upon the shaft 510 of the needle 180.

Figure 9:
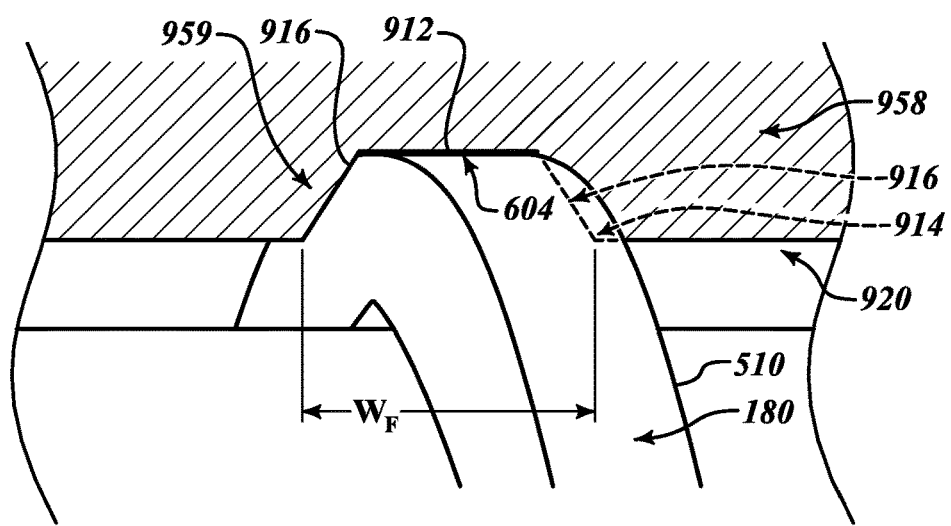
FIG. 9 is a side view of the needle of FIG. 5 received in a of a roller having a flared groove.

Referring additionally to FIG. 9, various embodiments of a grooved roller 958 may include a groove 959 that has two flared sides 916 to accommodate the shaft 512 of the needle 180. An object of the groove 959 with flared sides is to accommodate the sides of the needle 180. A square or rectangular groove without tapered sides may interfere with the needle 180 and cause the needle 180 to be deformed as the needle 180 rotates between the rollers. This tapered clearance is required to allow the helical needle to pass between the rollers 156 and 158 (FIG. 7) without with interference from the grooves. Thus, as shown in FIG. 9, the groove 959 flares from a bottom 912 of the groove 959 to an opening 914 at a surface 920 of the roller 958. Thus, the groove 959 has a generally trapezoidal cross-section. The width $W_F$ of the groove 959 at the surface 920 is used to accommodate sides 912 of the shaft 510 of the needle 180 as the shaft 510 of the needle 180 when the needle 180 is displaced or deformed.

Figure 10:
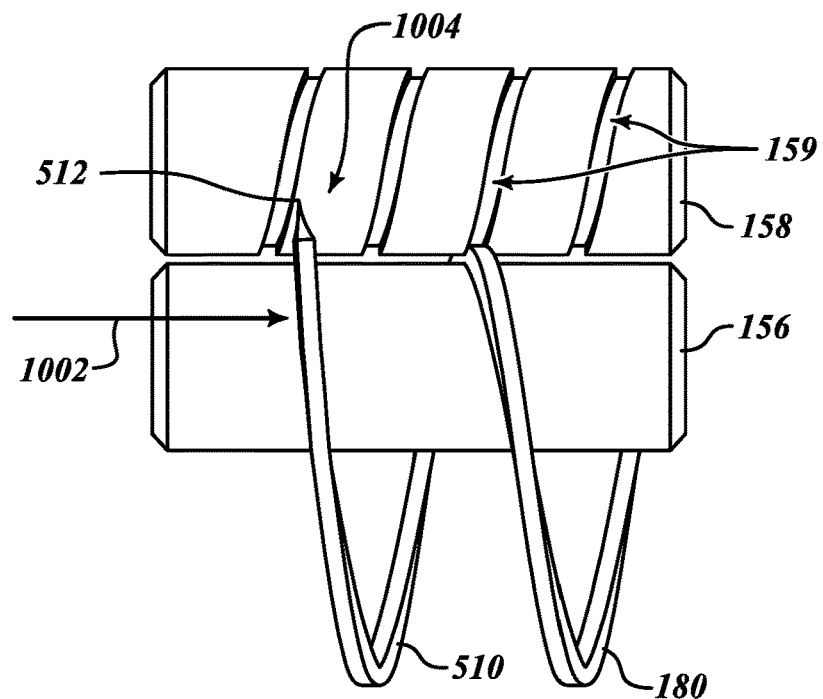
FIG. 10 is a schematic view of the rollers of the apparatus of FIG. 7 engaging the needle subject to a transverse force that compresses the needle.

Referring to FIG. 10, a force 1002 on the needle 180 also may cause the leading end 512 of the needle 180 to miss the groove 159 as the leading end 512 exits a body being sutured (not shown in FIG. 10) and revolves back toward the grooved roller 158. Instead of revolving into the groove 159, the leading end 512 of the needle 180 impacts upon a surface 1004 of the roller 158 outside of the groove 159. It will be appreciated that the force 1002 could act in either direction and thereby potentially cause the leading end 512 of the needle 180 to miss the groove 159 on either side.

Figure 11:
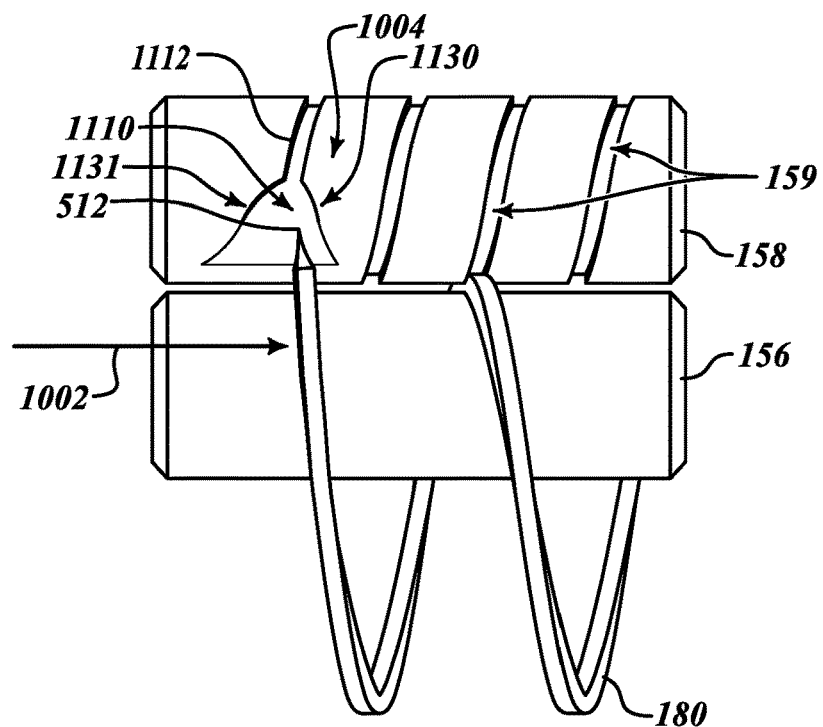
FIGS. 11-13 are schematic views of the rollers of the apparatus of FIG. 7 receiving the needle in a correcting recess.

Referring to FIG. 11, a correcting recess 1110 may be situated at a forward end 1112 of the groove 159 of the grooved roller 158. The correcting recess 1110 may be bounded by flared, lateral surfaces 1130 and 1131 that, as described below, will act as a funnel or guide to direct the leading end 512 of the needle 180 back into the groove 159. The lateral sides 1130 and 1131 define a widened area to receive the leading end 512 of the needle 180. Thus, the force 1002 does not act on the needle 180 (which would cause the leading end 512 of the needle 180 to miss the groove 159 and impact upon the surface 1004 of the roller 158). Instead, the leading end 512 of the needle 180 is received within the correcting recess 1110. Then, as described below, the counter-rotation of the rollers 156 and 158 will cause the correcting recess 1110 to rotate relative to the leading end 512 of the needle 180 to guide the needle 180 back into the groove 159.

Figure 12:
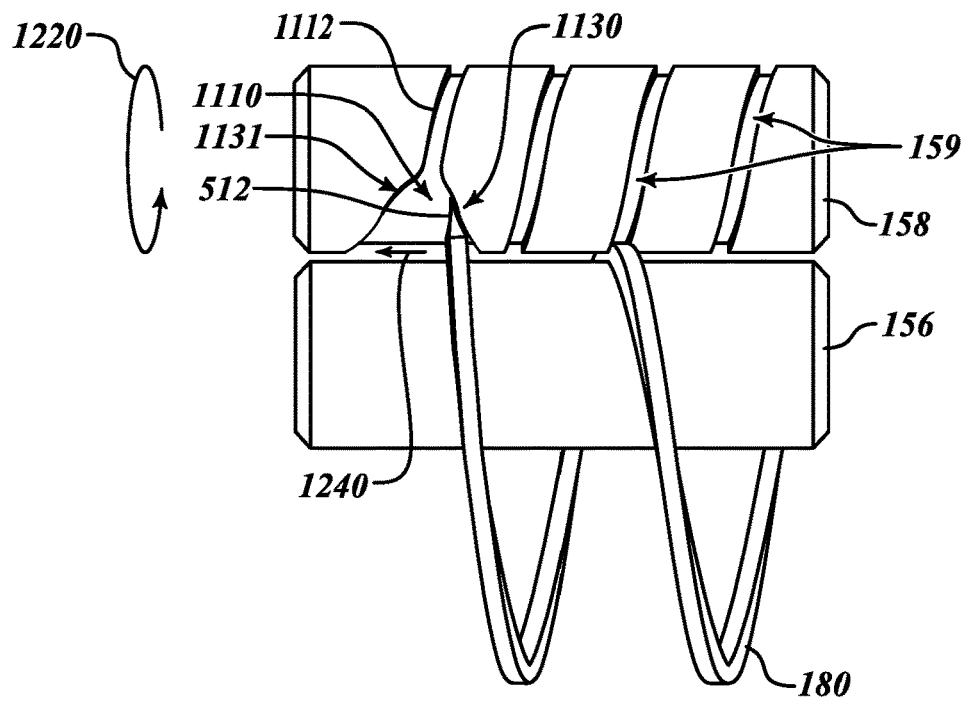

Referring to FIG. 12, as the rollers 156 and 158 counter-rotate with the grooved roller 158 rotating in a direction 1220, the correcting recess 1110 is rotated toward the opposing roller 156. The movement of the correcting recess 1110 results in the lateral surface 1130 of the correcting recess 1110 impinging upon the leading end 512 of the needle 180. The lateral surface 1130 moves the leading end 512 of the needle 180 in a direction 1240 to guide the leading end 512 toward the forward end 1112 of the groove 159.

Figure 13:
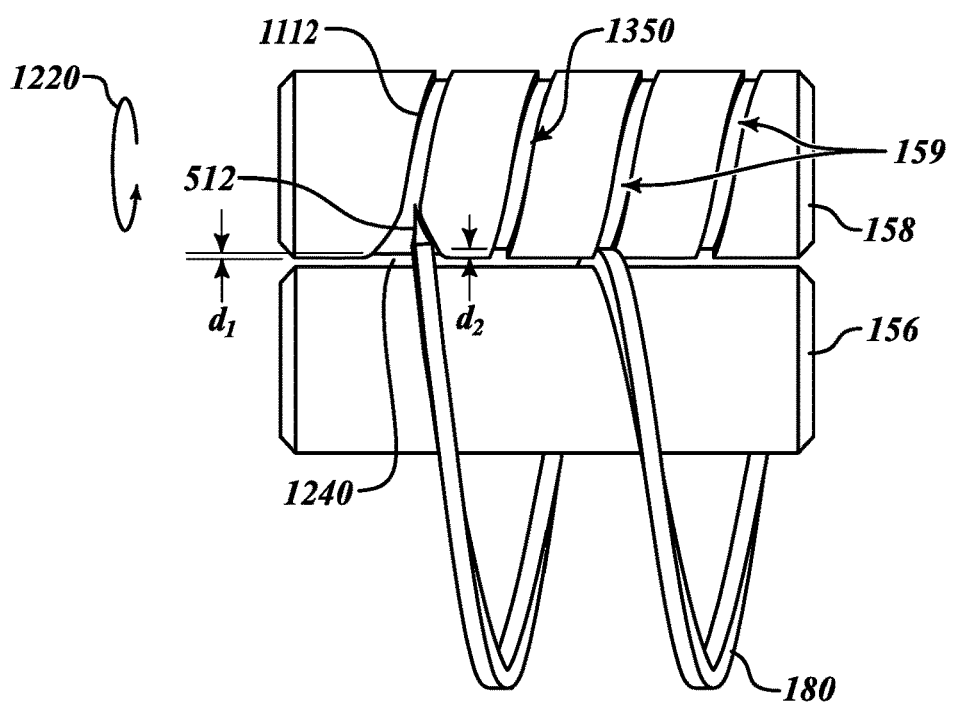

Referring to FIG. 13, with further rotation of the grooved roller 158 in the direction 1220, the leading end 512 of the needle is guided into the forward end 1112 of the groove 159. The correcting recess (not shown in FIG. 13) will repeatedly revolve into position to receive the leading end 512 of the needle 180 on a subsequent revolution of the needle 180 after forming each suture.

Still referring to FIG. 13, in various embodiments, the groove 159 may have a reduced depth $d_1$ at or near the forward end 1112 of the groove 159 as compared to a regular depth $d_2$ of a remaining portion 1350 of the groove 159. The reduced depth $d_1$ at the forward end 1112 may result in a reduced clearance between the forward end 1112 of the groove 159 and the opposing roller 156. Such reduced clearance could result in the opposing roller 156 applying higher pressure against the needle 180 at the forward end 1112 of the groove 159. The reduced depth $d_1$ (and the resultant higher pressure) enables the rollers 156 and 158 to securely grip the needle 180 as the needle 180 begins its next revolution after having been redirected into the groove 159 by the correcting recess 1110.

Figure 14:
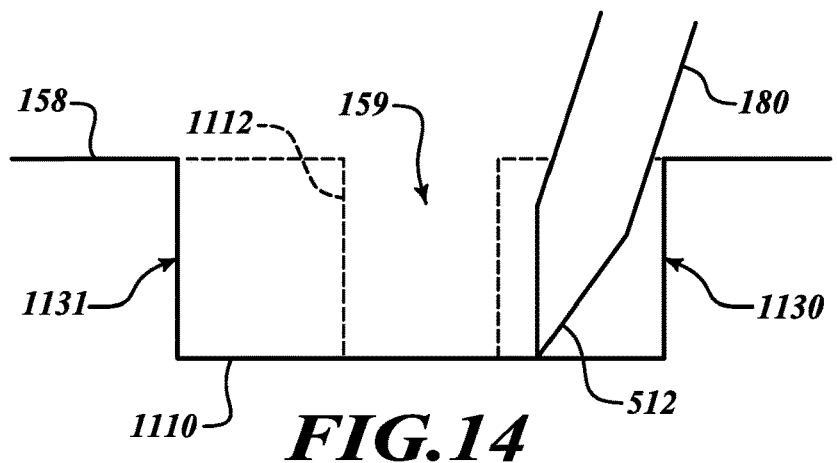
FIGS. 14-16 are side views of the needle being received by the correcting recess and guided into a groove.
Figure 15:
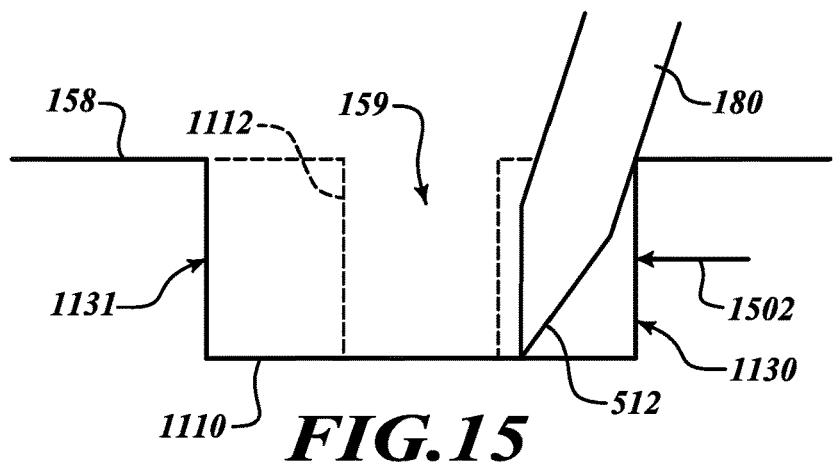
Figure 16:
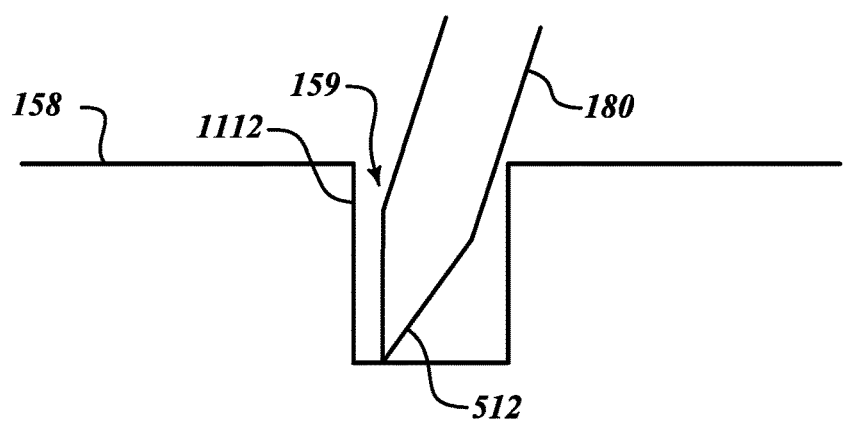

Referring to FIGS. 14-16, the leading end 512 of the needle 180 is directed by the lateral surface 1130 of the correcting recess 1110 into the forward end 1112 of the groove 159 of the grooved roller 158. Referring to FIG. 14, the leading end 512 of the needle 180 is received into the correcting recess 1110 between the lateral surfaces 1130 and 1131 that define the sides of the correcting recess 1110. As previously described with reference to FIG. 10, the leading end 512 of the needle 180 would have landed outside of the groove 159, the sides of which are represented by dotted lines in FIGS. 14-16.

Referring to FIG. 15, as the grooved roller 158 is rotated as described with reference to FIGS. 12 and 13, the lateral surface 1130 of the correcting recess 1110 engages the leading end 512 of the needle 180. It will be appreciated that, as the grooved roller 158 is rotated as described with reference to FIG. 13, the correcting recess 1110 narrows between the lateral surfaces 1130 and 1131. Referring to FIG. 16, as the grooved roller 158 is further rotated as described with reference to FIG. 13, the lateral surfaces 1130 and 1131 of the correcting recess 1110 (not shown in FIG. 16) merge into the forward end 1112 of the groove 159. Thus, the correcting recess 1110 receives the leading end 512 of the needle 180 at a location outside of the groove 159 and directs the leading end 512 of the needle 180 into the groove 159.

Figure 17:
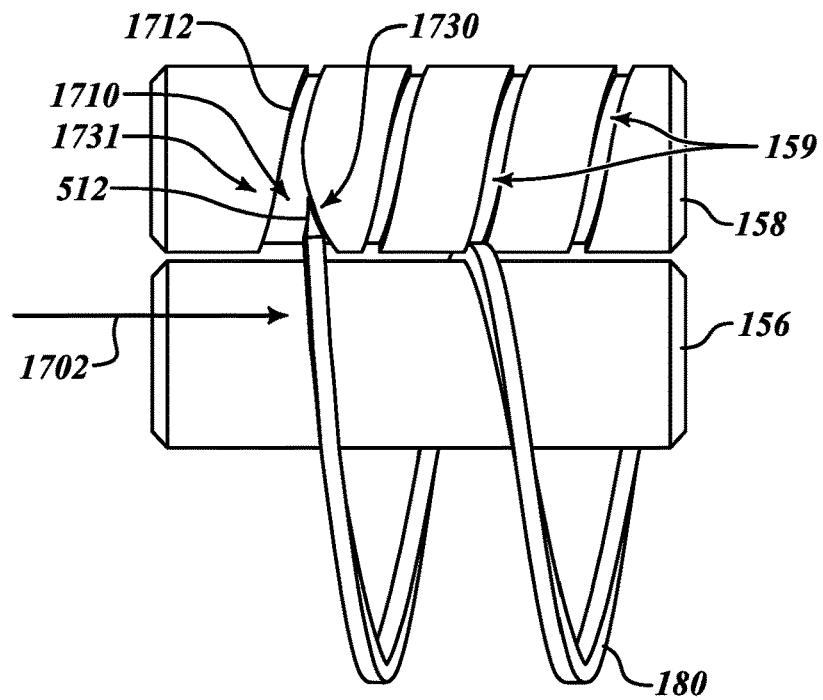
FIGS. 17 and 18 are schematic views of the grooved rollers of the apparatus of FIG. 7 employing other shapes of correcting recesses.
Figure 18:
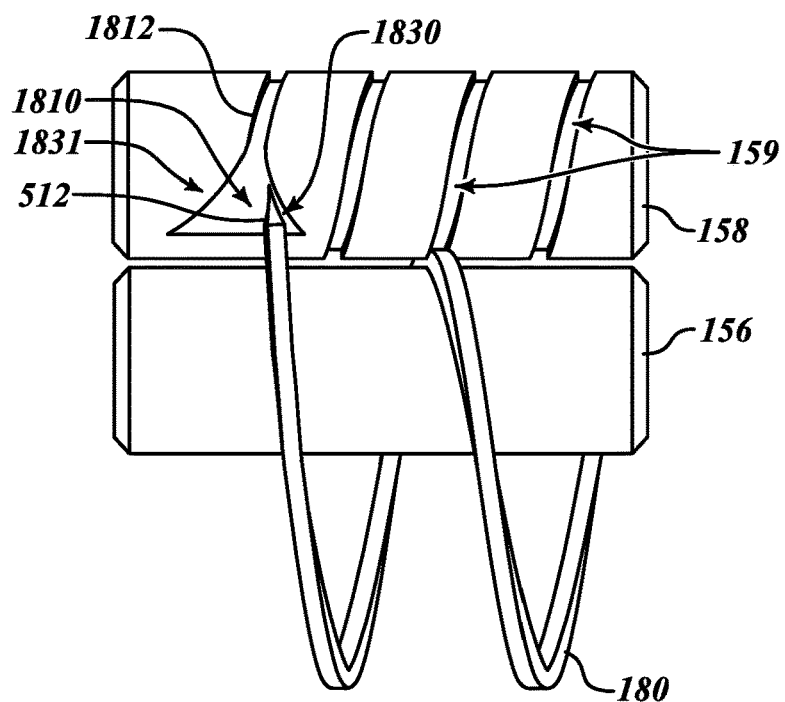

Referring to FIGS. 17 and 18, grooved rollers may include correcting recesses in other shapes than that described with reference to FIGS. 11-16. Referring to FIG. 17, for example, the grooved roller 158 may include a correcting recess 1710 that is only widened on one side. For example, it may be anticipated that the only forces acting on the needle 180 will deflect the needle 180 in a direction 1702. Thus, the correcting recess 1710 may include one lateral surface 1731 that extends straight from a forward end 1712 of the groove 159 and one flared lateral surface 1730 to accommodate deflection of the leading end 512 of the needle 180 in the direction 1702. The single flared lateral surface 1730 should accommodate any anticipated deflection of the leading end 512 of the needle 180.

It will be appreciated that the lateral surfaces of the correcting recess are not limited to straight, flared shapes. Referring to FIG. 18, for example, a correcting recess 1810 may include one or more curved or other non-straight surfaces 1830 and 1831 to engage the leading end 512 of the needle 180. The curved lateral surfaces 1830 and 1831 also may serve to impinge upon the leading end 512 of the needle 180 to guide the leading end 512 into the forward end 1812 of the groove 159. The lateral surfaces of the correcting recess are not limited to any particular geometric shape.

Figure 19A:
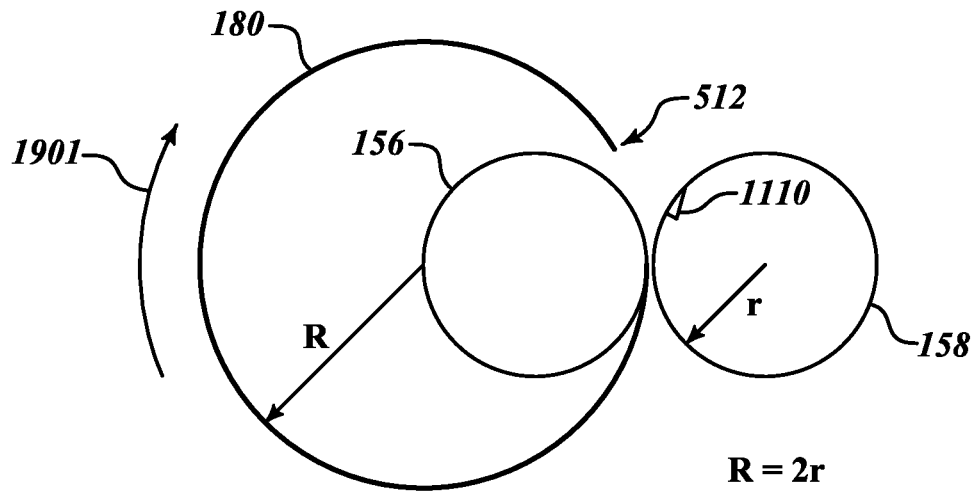
FIGS. 19A and 19B are schematic, axial views of a needle potentially missing the correcting recess on the grooved roller.
Figure 19B:
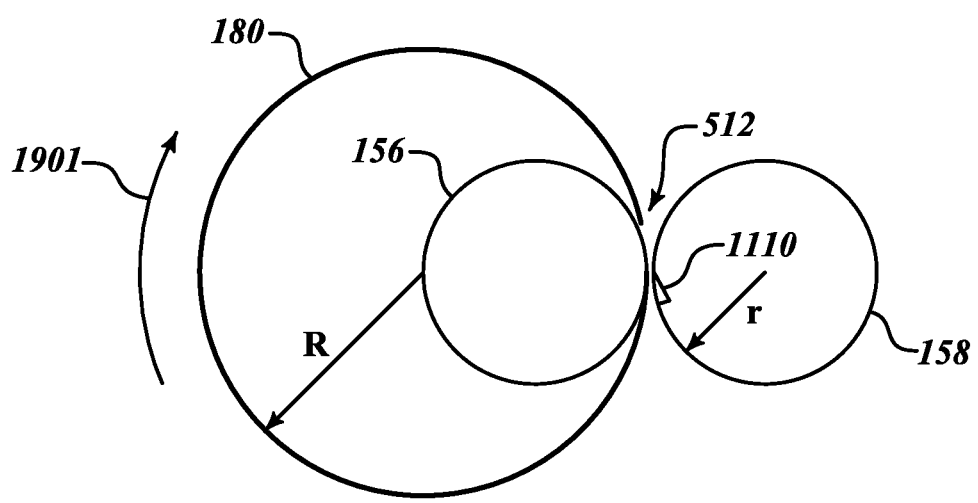

Referring to FIGS. 19A and 19B, based on forces that may affect movement of the helical needle 180, such as resistance encountered by the needle 180 or slippage of the needle 180 between rollers 156 and 158, may cause the leading end 512 of the needle 180 to miss the correcting recess 1110 when the leading end 512 rotates toward the correcting recess 1110.

Figure 20A:
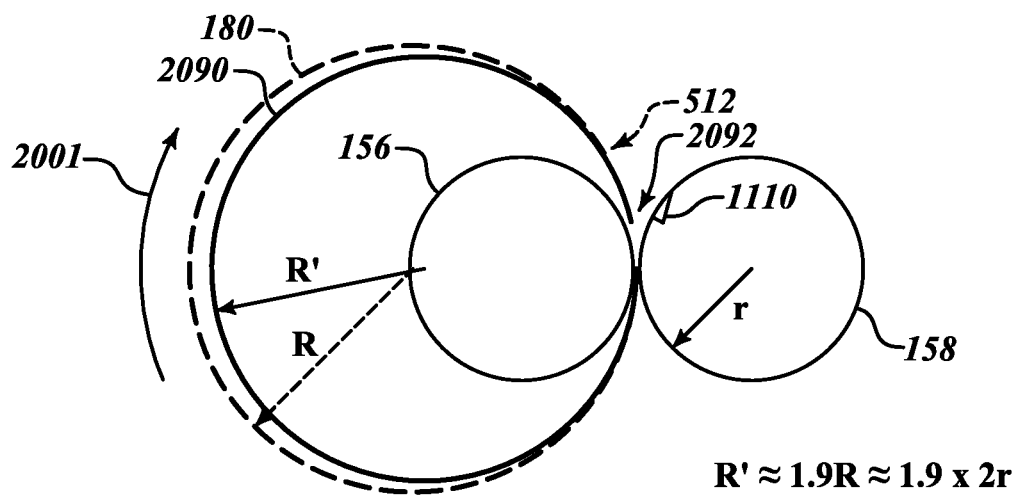
FIGS. 20A and 20B are schematic, axial views of a needle having a reduced helical radius.
Figure 20B:
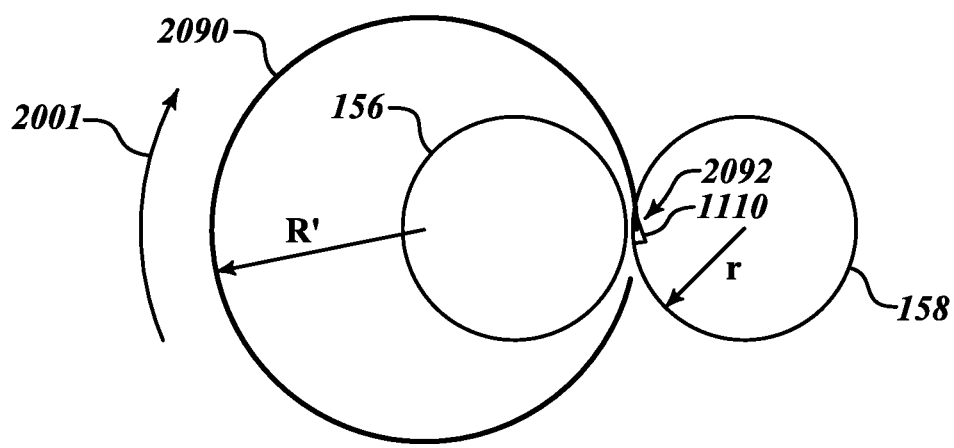

Referring to FIG. 19A, a portion of the needle 180 is depicted as the needle 180 revolves around the roller 156. It will be appreciated that the axial view of the needle 180 in FIGS. 19A and 19B, as well as the axial views of the needle 180 in FIGS. 20A and 20B, show a projection of the needle 180 that describe less than a full circular arc about their axes. In practice, however, the needle 180 actually describes more than a full circular arc around its axes to enable the rollers 156 and 158 to engage the shaft of the needle 180 as it fully revolves around its axis in forming sutures.

The needle 180 describes more than a full circular arc around its axis, in part, to account for the narrowed, sharpened leading end 512 of the needles 180, which may be too narrow to be engaged by the rollers 156 and 158. Similarly, the trailing end 514 (FIG. 5) of the needle 180 may be narrowed or tapered to engage the filament it draws that is used to form the sutures (not shown in FIGS. 29A-20B) may be too narrow to be engaged by the rollers 156 and 158. Accordingly, the needle 180 describes more than a full circular arc around its axis to allow for ends that may not be engageable by the rollers 156 and 158. In any case, the needle 180 in FIGS. 19A-20B is represented as not describing a full circular arc around its axis to be able to show a position of the leading end 512 of the needle 180 without the position of the leading end 512 potentially being obscured by an overlapping portion of the needle 180.

Continuing to refer to FIG. 19A, as the needle 180 revolves in a direction 1901 as a result of the counter-rotation of the rollers 156 and 158, the leading end 512 of the needle 180 approaches the correcting recess 1110 formed in the surface of the grooved roller 158. Referring to FIG. 19B, when some forces as described have impeded movement of the needle 180, the grooved roller 158 may have rotated such that the correcting recess 1110 has rotated such that the leading end 512 of the needle 180 is not received by the correcting recess 1110. Generally speaking, a radius R of the helical needle 180 will be a whole number multiple of the radius r of the grooved roller so that movement of the correcting recess 1110 is synchronized with the revolution of the needle 180 to receive the leading end 512 of the needle 180. In other words, a ratio between the radius R (or the diameter) of the needle 180 and the radius r (or the diameter) of the roller 158 will be a whole number that is greater than or equal to two. However, forces acting on the needle 180 may impair the synchronization of the rotation of the needle 180 and the grooved roller 158, thus indicating that the needle 180 have a radius R that may be less than a whole number multiple of the radius r of the roller 158 (or that the ratio of R to r should be less than two or another whole number ratio of R to r).

Referring to FIGS. 20A and 20B, reducing the radius of the helical needle 180 may compensate for forces that may impede rotation of the needle 180 to avoid synchronization problems with the grooved roller 158. Referring to FIG. 20A, the helical needle 2090 has a radius R' that is approximately five percent less than the radius R of needle 180 (represented in dashed line form in FIG. 20A for comparison with needle 2090). Thus, in contrast to the needle 180 having a radius R that is twice that of the radius r of the grooved roller 158, the needle 2090 has a radius R' that is approximately 1.9R, or five percent less than R. Having a shortened radius R', by contrast with the needle 180 of radius R, the leading end 2092 of the needle 2090 is closer to the grooved roller 158 at this point in the revolution of the needle 2090 than was the leading end 512 of the needle 180. Referring to FIG. 20B, as the needle 2090 revolves in a direction 2001, the leading end 2092 of the needle 2090 is received in the correcting recess 1110.

Figure 21A:
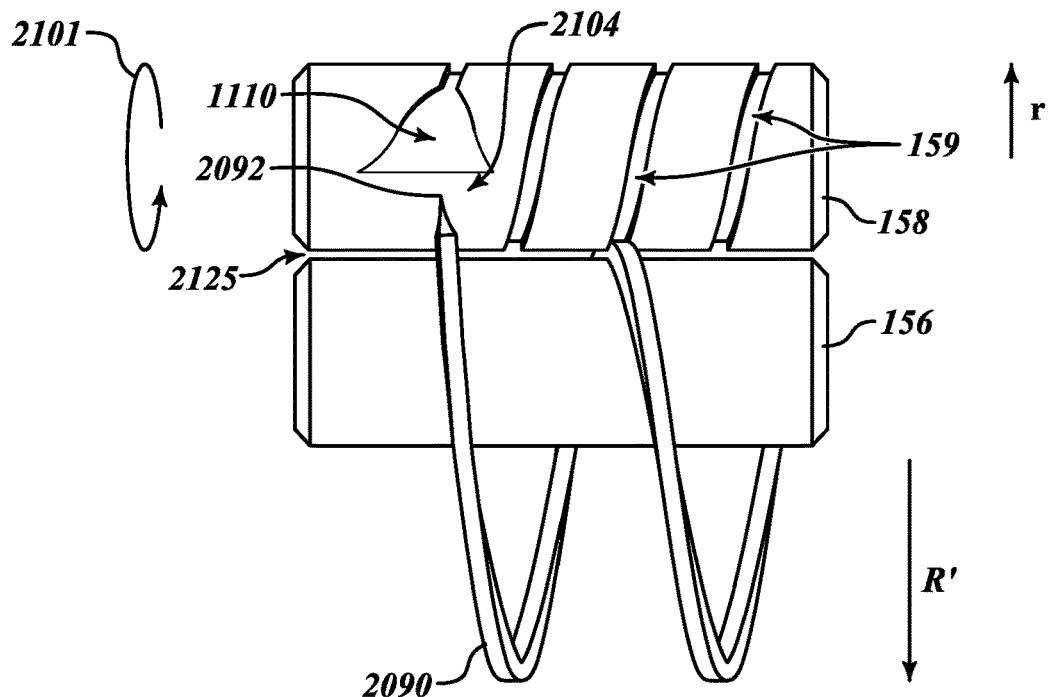
FIGS. 21A and 21B are schematic views of the needle of FIGS. 20A and 20B impacting on a surface of a grooved roller then being received in the correcting recess.
Figure 21B:
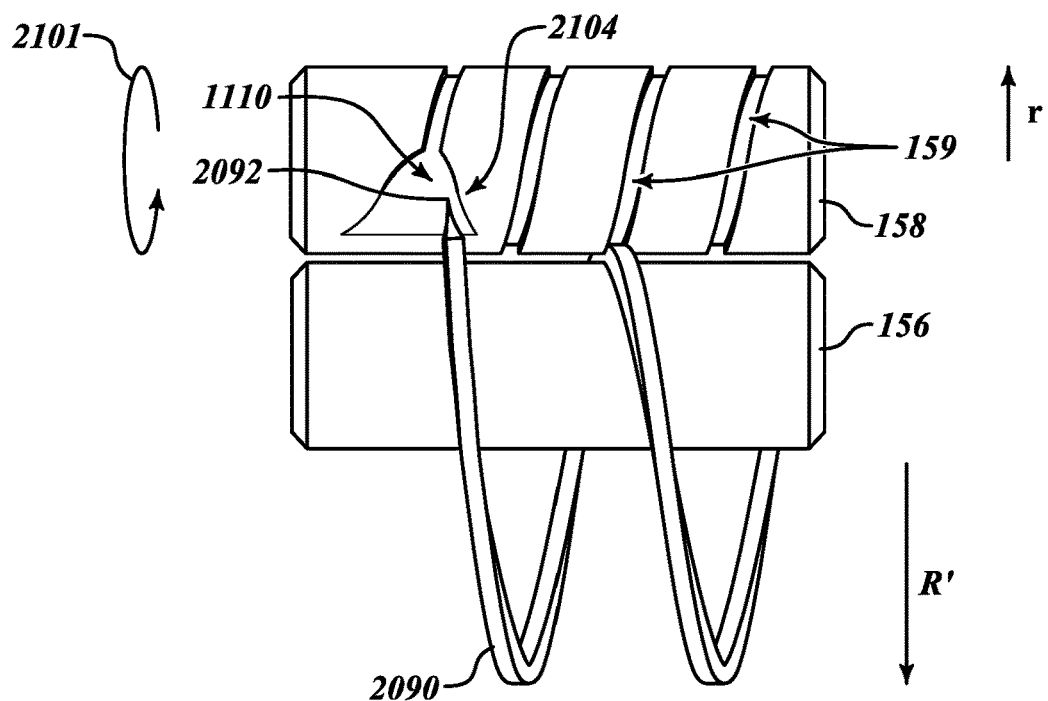

Referring to FIGS. 21A and 21B, a leading end 2092 of the needle 2090 may reach a surface 2104 of the grooved roller 158 before the correcting recess 1110 has been rotated into position to receive the leading end 2092 of the needle 2090. Because the needle 2090 has a radius R' that is less than a whole number multiple of the radius r of the grooved roller 158 as previously described, the needle 2090 may complete a revolution before the grooved roller with radius r, less than one-half that of the needle 2090 in this example, completes two rotations. Thus, it is possible that the leading end 2092 of the needle 2090 may reach the surface 2104 of the grooved roller 158 before the correcting recess 1110 is in position to receive the leading end 2092 of the needle 2090. Referring to FIG. 21A, the leading end 2092 of the needle 2090 may thus impact on the surface 2104 of the grooved roller 158 outside of the correcting recess 1110.

Referring to FIG. 21B, however, as the grooved roller 158 continues to revolve in a direction 2101 in counterrotation with the roller 156, the correcting recess 1110 rotates under the leading end 2092 of the needle 2090. Thus, even if the leading end 2092 of the needle 2090 with radius R' should be in position to engage the correcting recess 1110 before the correcting recess 1110 is in position to receive the leading end 2092, the leading end 2092 will slide along the surface 2104 of the grooved roller 158 until it can slide into the correcting recess 1110.

Even if the leading end 2092 should reach a gap 2125 (FIG. 21A) between the surface 2104 of the grooved roller 158 and the surface of the opposing roller 156 before the leading end 2092 is received into the correcting recess 1110, the needle 2090 cannot slip into the gap 2125 between the rollers 156 and '58. It will be recalled and appreciated that the helical needle 180 or 2090 is sized to fit between the rollers 156 and 158 only when received within the groove 159 of the grooved roller 159. Accordingly, the needle 2090 is too wide to fit into the gap 2125. Thus, the leading end 2092 of the needle 2090 will slide along the surface 2104 of the grooved roller 158 until the correcting recess 1110 rotates beneath the leading end 2092 of the needle 2090. At that point, the leading end 2092 of the needle 2090 will be captured by the correcting recess 1110 and guided into the groove 159 as previously described with reference to FIGS. 11-18.

Figure 22:
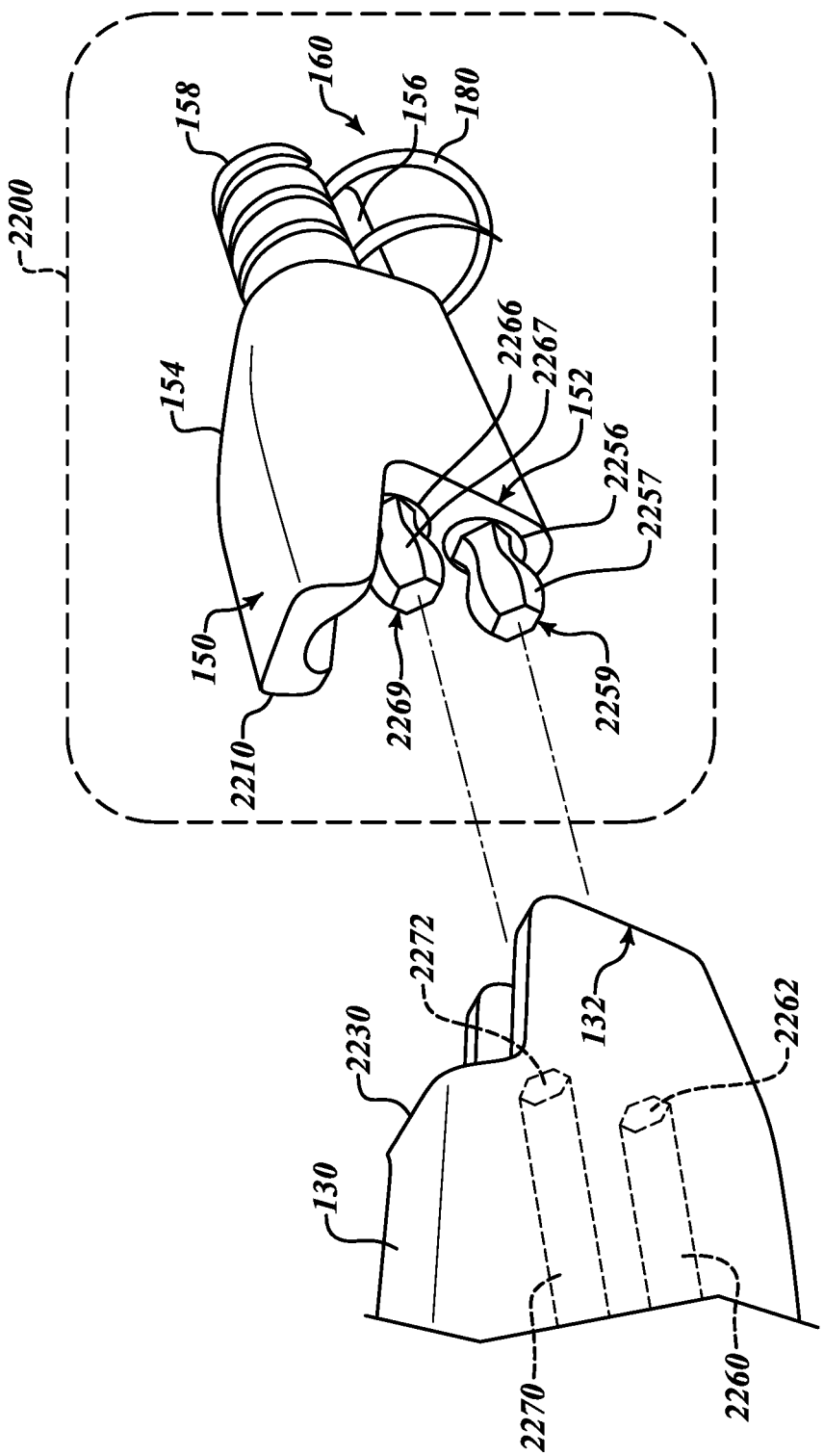
FIG. 22 is a perspective view of a shaft of the apparatus of FIG. 1 using a detachable suture cartridge.

In various embodiments, the roller mechanism 150 may be selectively detachable from and attachable to the motor drive 120. The roller mechanism 150 thus may be changed for sanitary reasons and/or, as further described below, to engage needles of different sizes. As previously described, a proximal end 152 of the frame 154 of the roller mechanism 150 engages a distal end 132 of the shaft 130. Referring additionally to FIG. 22, in various embodiments the roller mechanism 150 may thus be disengaged by detaching a juncture of the proximal end 152 of the roller mechanism 150 and the distal end 132 of the shaft 130. The roller mechanism 150, including the frame 154, rollers 156 and 158, and needle 180, may be regarded as a detachable and replaceable suture cartridge 2200. The distal end 132 of the shaft 130 thus may include a shaft coupling 2230 configured to engage a support coupling 2210 at the proximal end 152 of the frame 150. The couplings 2230 and 2210 may include a tongue-in-groove arrangement or another structure to frictionally and/or mechanically engage the distal end 132 of the shaft 130 with the proximal end 152 of the frame 154.

Still referring to FIG. 22, in various embodiments the shaft 130 may support one or more drive members 2260 and 2270 to convey rotational force from the motor 310 of the motor drive 110 (FIG. 3). The drive members 2260 and 2270 may include rigid or semi-rigid shafts or flexible drive cables. The drive members 2260 and 2270 may be coupled to the motor 310 in different ways. In various embodiments, the drive members 2260 and 2270 may be connected to a gear box (not shown) such that the drive members 2260 and 2270 counter-rotate in response to rotation of the motor 310 in order to counter-rotate the rollers 156 and 158, respectively. Other embodiments, may include only a single drive member 2260 or 2270 to convey rotational force from the motor 310 to one of the rollers 156 or 158. As previously mentioned, the rollers 156 and 158 may be coupled by a geared mechanism (not shown) housed at or within the frame 154 so that one of the rollers 156 or 158 receiving the rotational force from a drive member 2260 or 2270 will cause the other roller to counter-rotate. As also described, when one of the rollers 156 or 158 engages a drive member 2260 or 2270, frictional engagement of the rollers 156 and 158 with the needle 180 will cause the other of the rollers to counter-rotate. Any of these configurations may be used whether the roller mechanism 150 is fixably attached to the motor drive 110 or if the roller mechanism 150 is part of a suture cartridge 2200 detachable from the motor drive 110.

Particularly when the motor drive 110 is selectively detachable from and couplable with the suture cartridge 2200, the one or more drive members 2260 and 2270 must be detachable from and attachable to the rollers 156 and 158. In various embodiments, at least one of the rollers 156 and/or 158 includes a shaft 2256 and/or 2266, respectively, extending from the rollers 156 and/or 158 through the frame 154. The shafts 2256 and/or 2268 are engageable by the drive members 2260 and/or 2270, respectively. For purposes of the rest of this description, it will be understood that there may be one drive member 2260 or 2270 or two drive members 2260 and 2270 to engage one shaft 2256 or 2266 or two shafts 2256 and 2266, respectively.

To facilitate transfer of rotational force from the drive members 2260 and/or 2270 to the shafts 2256 and/or 2266, each of the shafts 2256 and/or 2266 may include a drive coupling 2257 and 2267, respectively. The drive couplings 2257 and 2267 include faceted ends 2259 and/or 2269. The faceted ends 2259 and/or 2269 may include shaped outer ends, such as hexagonal ends as shown in FIG. 22, or may include support geared surfaces or other ends suitable to receive rotational force via the drive members 2260 and/or 2270. The drive members 2260 and/or 2270 may include faceted ends 2262 and 2272 to engage the faceted ends 2259 and 2269, respectively, of the drive couplings 2266 and 2268. In various embodiments, the faceted ends 2262 and 2272 of the drive members 2260 and 2270, respectively, may include inner-facing sockets to engage outer-facing ends of the drive couplings 2257 and 2267, respectively. Thus, when the motor drive 110 is engaged with the suture cartridge 2200, with the distal end 132 of the shaft 130 engaging the proximal end 152 of the frame 150, the faceted ends 2262 and/or 2272 of the drive members 2260 and/or 2270 engage the faceted ends 2259 and 2269 of the drive couplings 2257 and/or 2267, respectively.

As previously mentioned, when interchangeable suture cartridges 2200 are used, different cartridges may have differently-sized needles for different applications. For example, a suture cartridge having a needle with a smaller helical radius may be used to form a small suture to close small wounds or incisions. Alternatively, a suture cartridge having a needle with a larger helical radius may be used to form a larger suture to close larger wounds or incisions. the suture cartridges may have differently-sized rollers. To accommodate differently-sized needles, pitches of the grooves of the grooved rollers and pitches of the needle should be ratiometrically matched to ensure proper alignment of the needle with the grooves as the grooved roller is rotated. In addition, it may be desirable to use differently-sized rollers to support differently-sized needles. For example, to suture a small incision, a needle with a small helical radius may be desirable so that the suture closely matches edges of the wound or incision to be closed. Accordingly, at least the roller about which the needle revolves should have a smaller radius to accommodate the needle having a smaller helical radius. Correspondingly, when a larger needle is desired to form a suture to close a larger wound or incision, larger rollers may be desired to provide a wider surface with which to frictionally engage the needle as the needle is revolved to form the suture.

Figure 23:
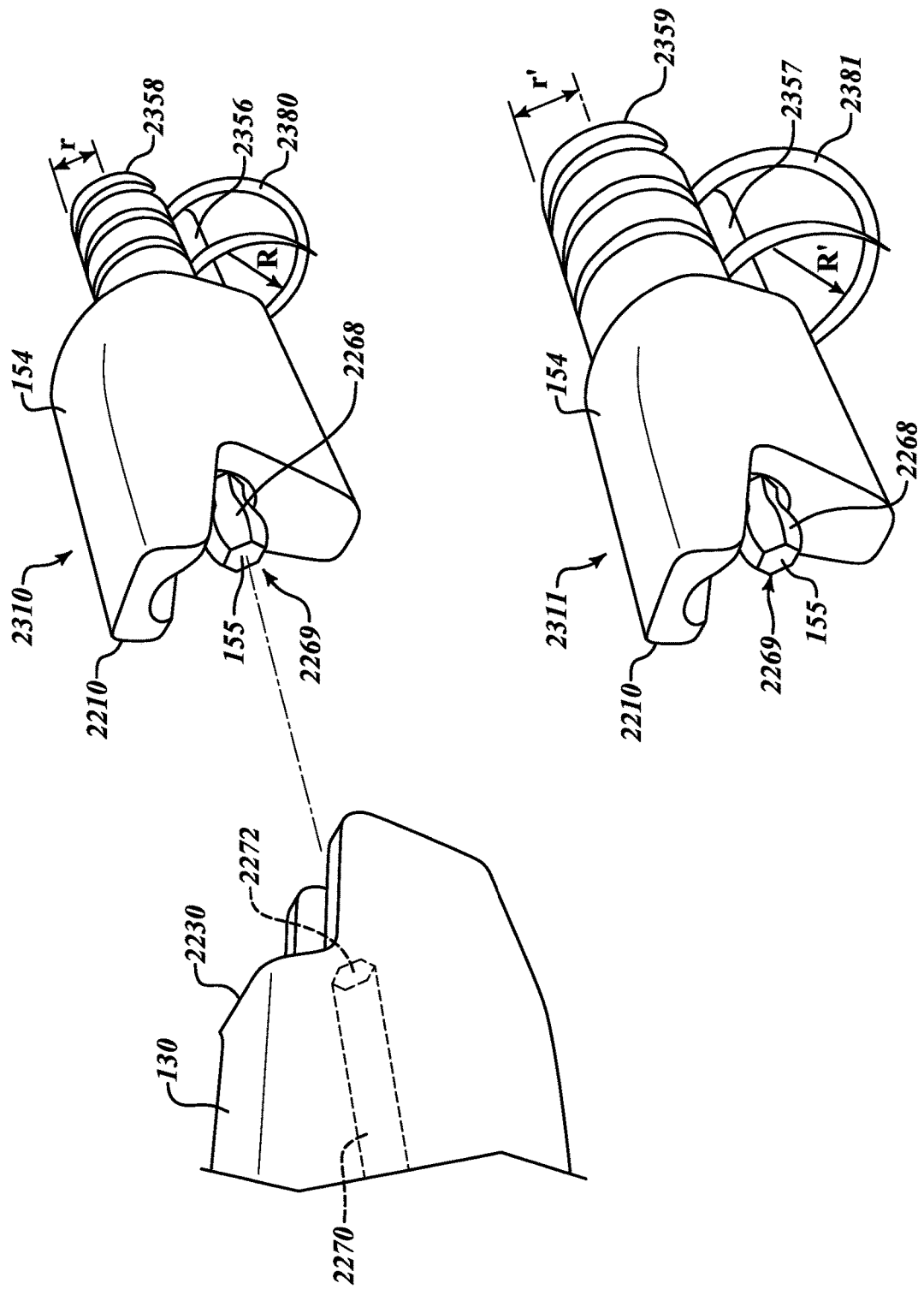
FIG. 23 is a perspective view of a shaft of the apparatus of FIG. 1 engageable with alternative suture cartridges having differently-sized needles.

Referring to FIG. 23, suture cartridges 2310 and 2311 of two different sizes support different sizes of needles 2380 and 2381 having different helical radii R and R', respectively. Each of the suture cartridges 2310 and 2311 includes the support coupling 2210 configured to engage the shaft coupling 2230 of the shaft 130 so that the suture cartridges 2310 and 2311 may be mechanically supported by the shaft 130. Both suture cartridges 2310 and 2311 include frames 154 of the same size. However, it will be appreciated that the frames of the suture cartridges 2310 and 2311 need not be of the same size as long as the frames are equally capable of engaging the shaft 130.

Both suture cartridge 2310 and 2311 include the shaft 2268 having the faceted end 2269 to engage the faceted end 2272 of the drive member 2270 to provide rotational force to the rollers. In contrast to the suture cartridge 2200 of FIG. 1, the suture cartridges 2310 and 2311 are motivated by the single drive member 2270, with gears between the rollers or frictional engagement with the needle causing both rollers to counter-rotate, as previously described. The shaft 2268 and the faceted end 2269 of both suture cartridges 2310 and 2311 are equivalent to support interchangeability of the suture cartridges 2310 and 2311 with the drive member 2270.

The suture cartridge 2310 has a grooved roller 2358 with a radius r and an opposing roller 2356 around which revolves a needle 2380 of helical radius R. The suture cartridge 2311 has a grooved roller 2359 with a radius r' and an opposing roller 2357 around which revolves a needle 2381 of helical radius R'. The helical radius R' is greater than the helical radius R such that the suture cartridge 2311 is suited to form a larger suture than the suture cartridge 2310. In the case of both the suture cartridge 2310 and the suture cartridge 2311, the pitches of the grooves in the grooved rollers 2358 and 2359 and the helical needles 2380 and 2381, respectively, are ratiometrically matched. The diameters r and r' are selected to cause the needles 2380 and 2381, respectively, to revolve to form a single suture when the motor drive (not shown in FIG. 23) is engaged to cause the needle 2380 or 2381 to revolve. In various embodiments, the rollers 2356 and 2357 about which the needles 2380 or 2381 revolve, respectively, may be of the same size or of different sizes, provided that the rollers 2356 and 2357 provide suitable frictional engagement with the needles 2380 and 2381 to motivate revolution of the needles 2380 and 2381.

Although suture cartridges 2310 and 2311 of only two sizes are shown, it will be appreciated that there could be suture cartridges of any number of sizes to form sutures of any size. In addition, although not shown in FIG. 22, each of the needles 2380 and 2381 would be joined with a filament to effect formation of sutures.

Figure 24:
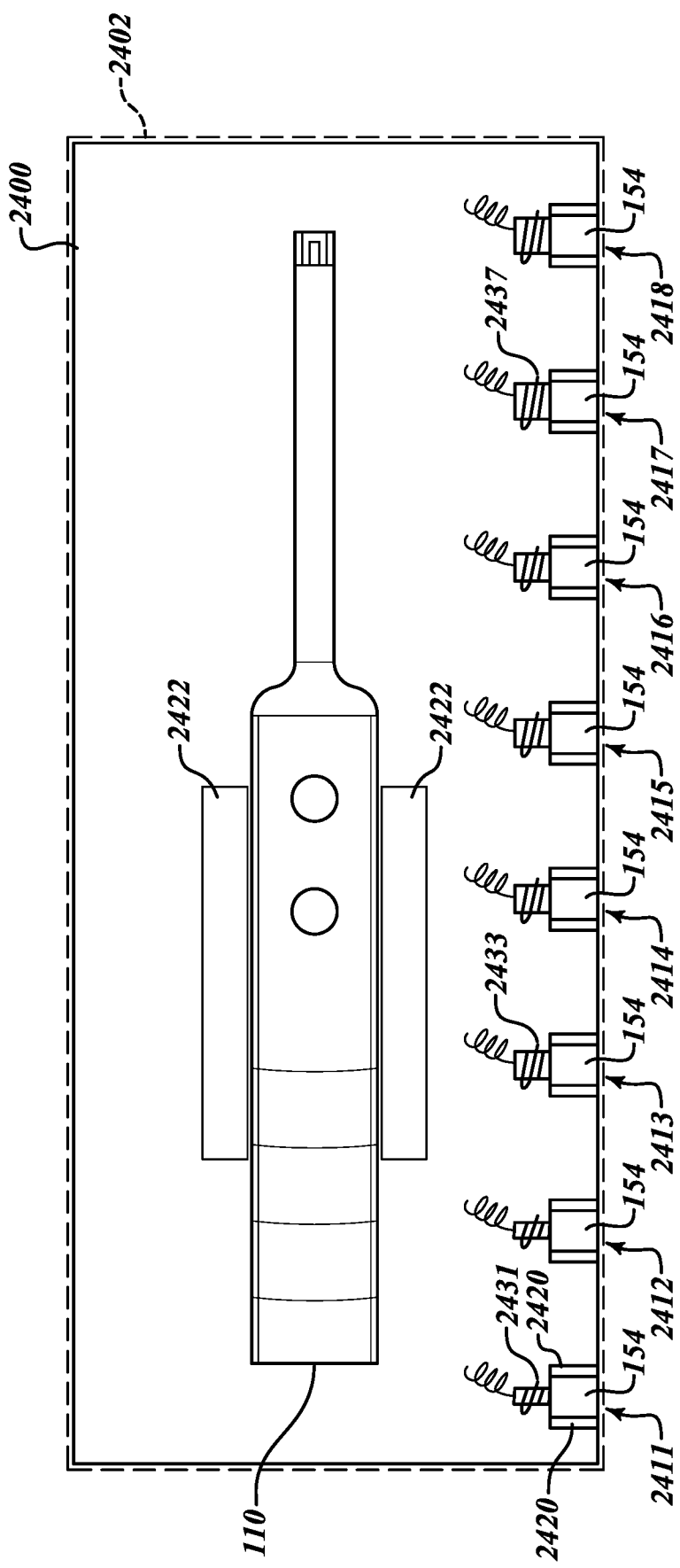
FIG. 24 is a top-down view of a supply tray that supports a motor drive of the apparatus of FIG. 1 and a number of interchangeable suture cartridges.

Referring additionally to FIG. 24, a supply tray 2400 supports a number of interchangeable suture cartridges 2411-2418. The supply tray 2400 may include brackets 2420 to frictionally engage sides of the suture cartridges to hold the suture cartridges 2411-2418 in place until they are engaged by the motor drive 110 and dislodged from the supply tray 2400 for use. As described further with reference to FIG. 24, in various embodiments, the supply tray 2400 supports the suture cartridges 2411-2418 with the support couplings and drive couplings (not shown in FIG. 24) presented so that the motor drive 110 may engage any of the suture cartridges 2411-2418 without a user having to handle or touch the supply cartridges 2411-2418. The user not having to handle or touch the supply cartridges 2411-2418 may prevent the suture cartridges 2411-2418 from being soiled or infected with germs or other matter from the user's hands. To this end, the supply tray 2400 may be covered with a sanitary wrapping 2402 (represented by dashed lines) to seal the supply tray. Similarly, the motor drive 110 (which also may be held to the surface of the supply tray 2400 by brackets 2422) may be presented sanitarily on the supply tray 2400.

The suture cartridges 2411-2418 supported by the supply tray 2400 may be of different sizes to enable the operator to select an appropriate suture cartridge or cartridges for a present application. For example, the suture cartridge 2410 includes a smaller needle 2431 (and, thus, potentially smaller rollers, as previously described) than the needle 2433 of the suture cartridge 2413. Similarly, the suture cartridge 2417 includes a larger needle 2437 than the needle 2433 of the suture cartridge 2413. The operator thus may select from among the available suture cartridges 2411-2418 to choose the suture cartridge that will form a suture of the size appropriate to the present application.

Figure 25:
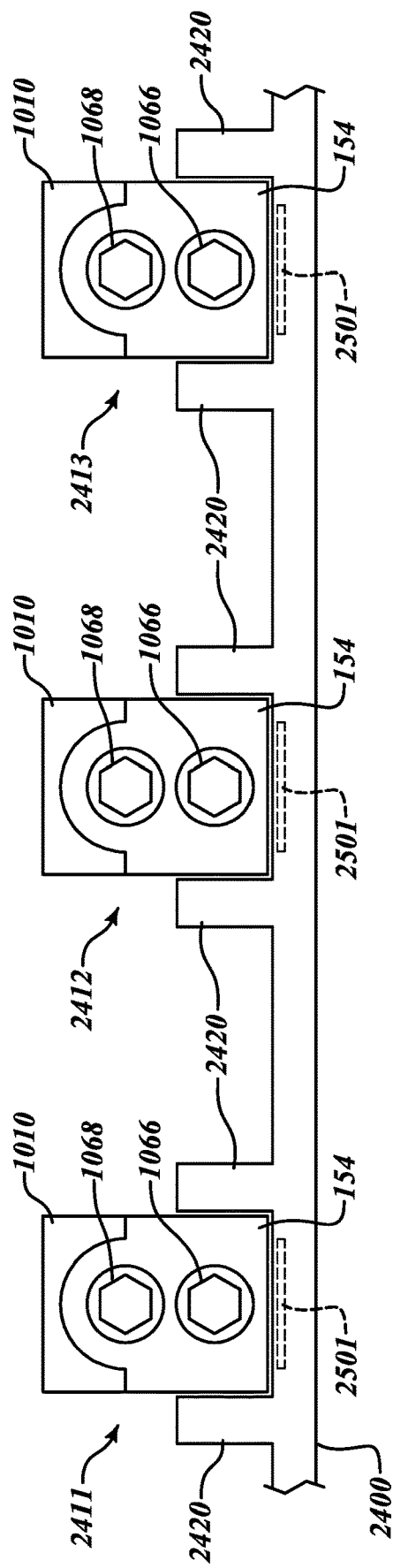
FIG. 25 is a side view of a portion of the supply tray of FIG. 24 that supports interchangeable suture cartridges.

Referring additionally to FIG. 25, the supply tray 2400 presents ends of the suture cartridges 2411-2413 with each of their support couplings 2210 and drive couplings 2266 and 2268 presented to be accessible by the motor drive 110. As shown in FIG. 24, the suture cartridges 2411-2413 are mechanically held to the supply tray 2400 with brackets 2420 holding each of the suture cartridges 2411-2413 therebetween. Alternatively or additionally, the supply tray 2400 may include a base 2501 that forcibly engages the frame 154 of each of the suture cartridges 2411-2413 to hold the suture cartridges 2411-2413 in place. For example, the base 2501 may be an adhesive pad or a magnet configured to engage the frame 154 of each of the suture cartridges 2411-2413 to hold the suture cartridges 2411-2413 in place until engaged by the motor drive 110 to remove it from the supply tray 2400.

Figure 26A:
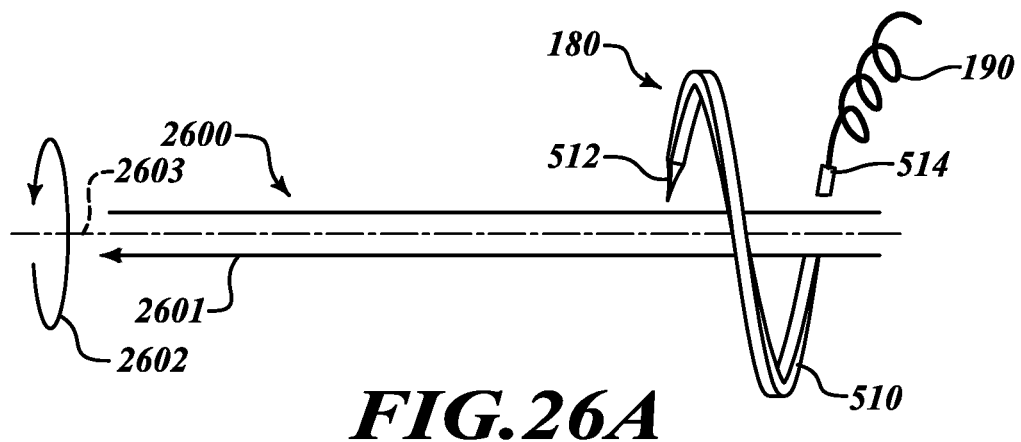
FIG. 26A is schematic diagram of a helical needle positioned to suture an opening.
Figure 26B:
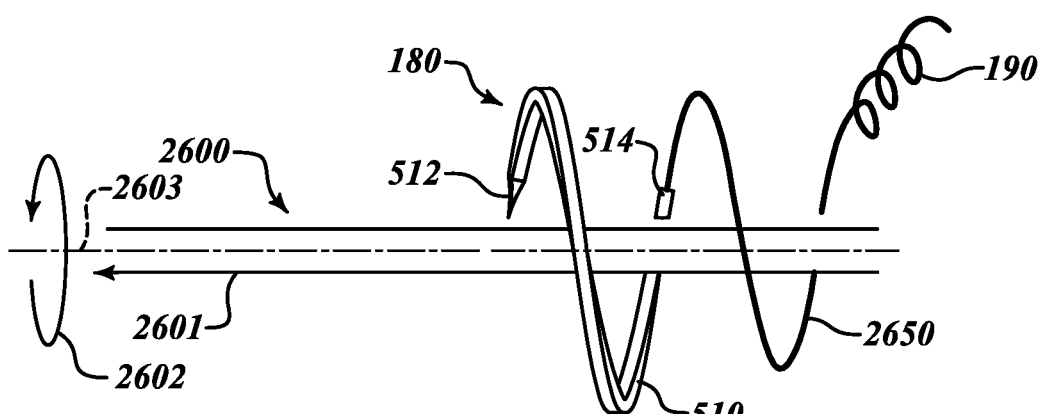
FIG. 26B is a schematic diagram of the helical needle of FIG. 26B after it has been revolved to suture the opening.

Referring additionally to FIGS. 26A and 26B, the revolution of the needle 180 by the rollers (not shown in FIGS. 26A and 26B) forms a suture 2650 to close an opening 2601 in a body 2600, such as a wound or incision. As shown in FIG. 26A, the needle 180 is about to be revolved in the direction 2602 to pierce the body 2600 adjacent the opening

2601. Because the needle 180 is helical in shape, revolution of the needle 180 causes the needle 180 to be drawn in the direction 2603. The leading end 512 of the needle 180 pierces the body 2600. Revolution of the needle 180 draws the shaft 510 of needle 180 through the body until the trailing end 514 drawing the filament 190 emerges from the body 400. As shown in FIG. 26B, after the needle 180 is revolved in the direction 2602 and, thus, moved in the direction 2601, a loop of the filament 190 has formed a suture 2650 through the body 2600.

Figure 27:
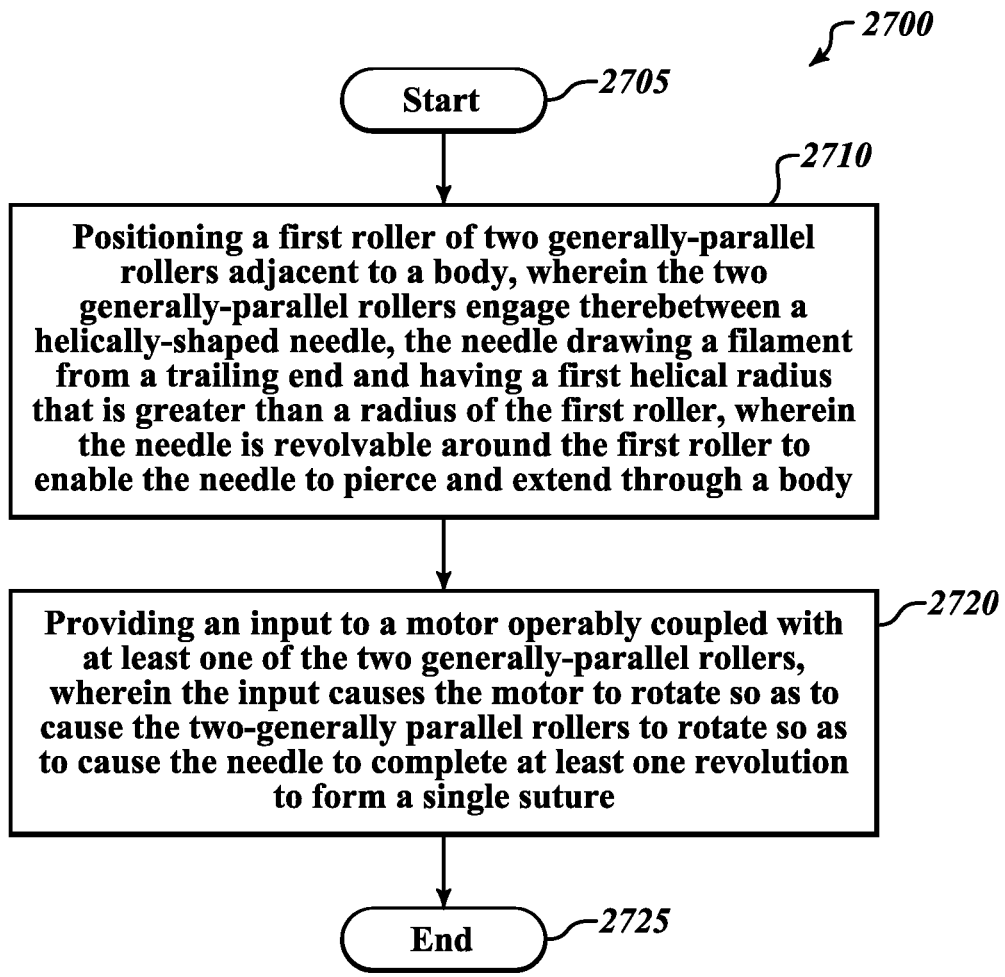
FIG. 27 is a flow chart of an illustrative method of suturing a body with a helically-shaped needle motivated by two generally-parallel rollers.

Referring additionally to FIG. 27, in various embodiments an illustrative method 2700 is provided for suturing an object by revolving a helical needle as previously described. The method 2700 starts at a block 2705. At a block 2710, a first roller of two generally-parallel rollers is positioned adjacent to a body, wherein the two generally-parallel rollers engage therebetween a helically-shaped needle. The needle draws a filament from a trailing end and having a first helical radius that is greater than a radius of the first roller and the needle is revolvable around the first roller to enable the needle to pierce and extend through a body. At a block 2720, an input is provided to a motor operably coupled with at least one of the two generally-parallel rollers. The input causes the motor to rotate so as to cause the two-generally parallel rollers to rotate so as to cause the needle to complete at least one revolution to form a single suture. The method 2700 ends at a block 2725.

Figure 28:
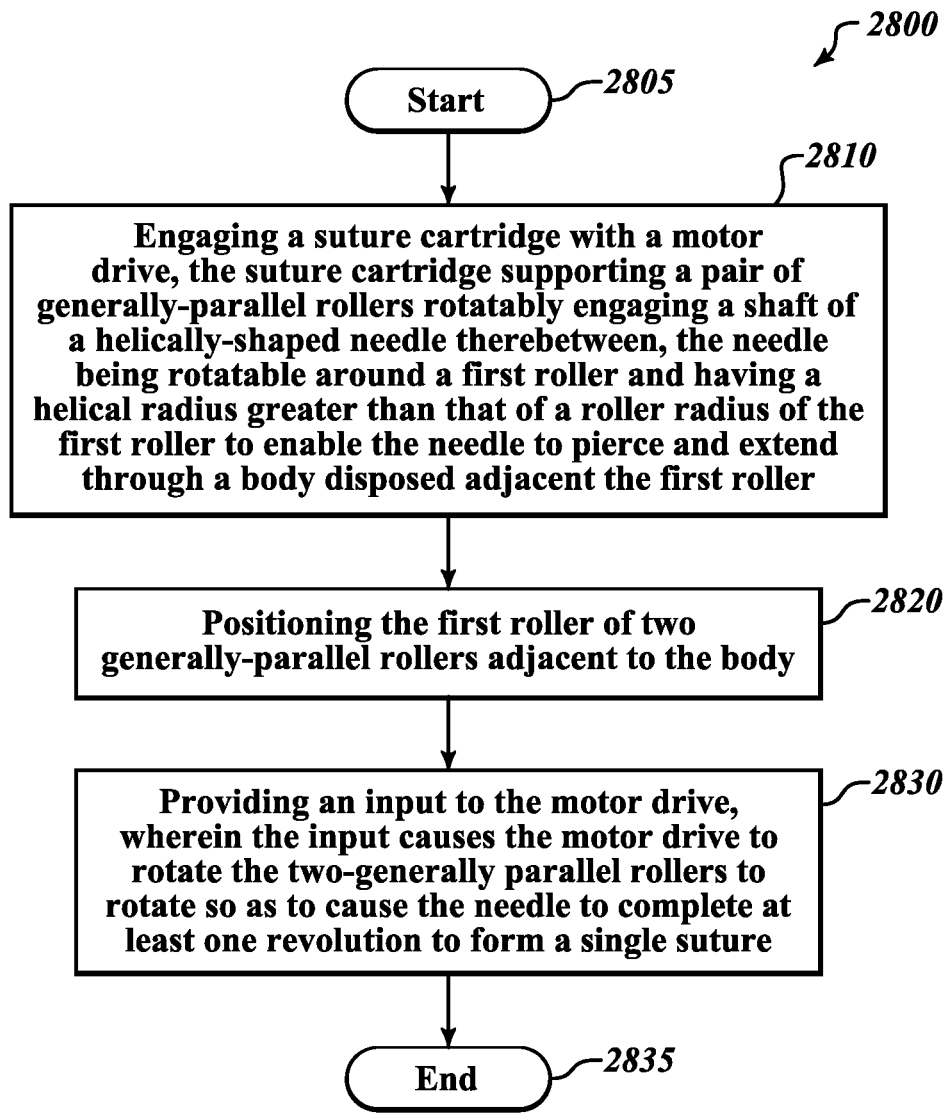
FIG. 28 is a flow chart of an illustrative method of engaging a suture cartridge with a motor drive to suture a body.

Referring additionally to FIG. 28, in various embodiments an illustrative method 2800 is provided for using an interchangeable suture cartridge to form a suture. The method 2800 starts at a block 2805. At a block 2810, a suture cartridge is engaged with a motor drive, the suture cartridge supporting a pair of generally-parallel rollers rotatably engaging a shaft of a helically-shaped needle therebetween. The needle is rotatable around a first roller and has a helical radius greater than that of a roller radius of the first roller to enable the needle to pierce and extend through a body disposed adjacent the first roller. At a block 2820, the first roller of two generally-parallel rollers is positioned adjacent to the body. At a block 2830, an input is provided to the motor drive, wherein the input causes the motor drive to rotate the two-generally parallel rollers to rotate so as to cause the needle to complete at least one revolution to form a single suture. The method 2800 ends at a block 2835.

It will be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. A suture cartridge apparatus configured to be coupled to a drive mechanism via an elongate shaft, the apparatus comprising:
    a helically-shaped needle having a first helical radius, the needle having a shaft and drawing a filament from a trailing end;
    two generally-parallel counter-rotating rollers configured to engage therebetween the shaft of the needle, the two generally-parallel counter-rotating rollers including a first non-grooved roller, and a second grooved roller positioned adjacent the first non-grooved roller and configured to be opposite a body during use of the suture cartridge, the second grooved roller including a correcting recess to guide the helically-shaped needle into a groove, wherein the correcting recess is positioned at a leading end of the groove to direct a leading end of the helically-shaped needle into the groove;
    a frame configured to counter-rotatably support the rollers and including:
    a support coupling configured to detachably receive a shaft coupling on a distal end of the elongate shaft extending from the drive mechanism; and
    a drive coupling forming a proximal end of a roller shaft extending from one roller of the two generally-parallel counter-rotating rollers, the drive coupling configured to receive a rotational force input from the drive mechanism and transfer the rotational force to the roller shaft.

2. The apparatus of claim 1, wherein the support coupling includes a tongue portion of a tongue-in-groove arrangement configured to mate with a groove portion of the shaft coupling.

3. The apparatus of claim 1, wherein the drive coupling includes a shaft extending from an end of one of the rollers and having a faceted end configured to detachably engage the drive mechanism.

4. The apparatus of claim 1, wherein the frame is engageable by a supply tray, wherein the supply tray is configured to apply force to the frame to hold the frame in place unless the support shaft engages the frame and dislodges the frame from the supply tray.

5. The apparatus of claim 1, wherein:
    the first roller includes a flat surface configured to rollably engage a first side of the shaft of the needle; and
    the groove is configured to at least partially receive a second side of the shaft of the needle.

6. The apparatus of claim 5, wherein a pitch of the groove is ratiometrically matched to a pitch of the needle according to a ratio of a radius of the needle to a radius of the second roller.

7. The apparatus of claim 1, wherein the frame includes an open distal end at an end opposite the support coupling and wherein the needle is received between the rollers with the trailing end of the needle facing the open distal end to draw the filament from the open distal end.

8. The apparatus of claim 1, wherein the correcting recess is connected to the leading end of the groove via opposing flared lateral surfaces.

9. The apparatus of claim 1, wherein the correcting recess includes a widened opening that tapers into the groove at the leading end of the groove.

10. The apparatus of claim 1, wherein the correcting recess is positioned at the leading end of the groove such that the correcting recess will repeatedly revolve into a position to receive a leading end of the helically-shaped needle.

11. A system comprising:
    a drive mechanism including:
    a housing;
    a motor supported by the housing;
    a support shaft including an elongated body extending from the housing; and
    a drive member coupled with the motor and supported by the shaft while extending a length of the elongate body, the drive member being configured to convey rotational force from the motor; and
    a suture cartridge including:
    a helically-shaped needle having a first helical radius, the needle having a shaft and drawing a filament from a trailing end;
    two generally-parallel counter-rotating rollers configured to engage therebetween the shaft of the needle, a first roller of the two generally-parallel counter-rotating rollers having a roller radius that is less than the helical radius of the needle to enable the needle to revolve around the first roller to pierce a body disposed adjacent the first roller and to draw the filament through the body, wherein one of the two generally-parallel counter-rotating rollers includes a correcting recess disposed at a forward end of a groove to guide the helically-shaped needle into the groove; and a frame configured to counter-rotatably support the rollers and including:

a support coupling configured to detachably receive a shaft coupling on a distal end of the support shaft; and a drive coupling configured to receive a rotational force from the drive member to convey the rotation force to at least one of the two generally-parallel counter-rotating rollers.

12. The system of claim 11, further comprising a suture controller wherein, in response to a user input, the suture controller causes the motor to rotate through a number of revolutions to cause the needle to complete at least one revolution to form a single suture.

13. The system of claim 11, further comprising a plurality of switchable suture cartridges configured to interchangeably receive the support shaft and the drive member of the drive mechanism.

14. The system of claim 13, wherein the plurality of switchable suture cartridges includes differently-sized cartridges, wherein each of the differently-sized cartridges supports a needle having a different helical radius, wherein each of the plurality of switchable suture cartridges is configured to form a suture of a differing size.

15. The system of claim 14, wherein the first roller of the differently-sized cartridges have different roller radii.

16. The system of claim 14, wherein the drive coupling of each of the suture cartridges is configured to cause the needle to complete at least one revolution to form a single suture independent of a size of the helical radius of the needle.

17. The system of claim 16, wherein the drive coupling includes at least one faceted member coupled with one of the rollers to receive a faceted end of the drive member.

18. The system of claim 11, wherein:

the first roller of the two generally-parallel counter-rotating rollers includes a flat surface configured to rollably engage a first side of the shaft of the needle; and a second roller of the two generally-parallel counter-rotating rollers includes a grooved surface defining the groove that is configured to at least partially receive a second side of the shaft of the needle.

19. The system of claim 18, wherein a pitch of the groove is ratiometrically matched to a pitch of the needle according to a ratio of a radius of the needle to a radius of the second roller.

20. The system of claim 11, wherein the suture cartridge includes an open distal end wherein ends of the two generally-parallel rollers are exposed, wherein with the trailing end of the needle facing the open distal end to draw the filament from the open distal end.

21. A method comprising:

engaging a suture cartridge with a motor drive, the suture cartridge supporting a pair of generally-parallel counter-rotating rollers rotatably engaging a shaft of a helically-shaped needle therebetween, the needle being rotatable around a first non-grooved roller and the needle being guided into a groove in a second grooved roller by a correcting recess disposed at a forward end of the groove;

positioning the first non-grooved roller of the pair of generally-parallel rollers adjacent to a body and the second grooved roller of the pair of generally-parallel counter-rotating rollers adjacent the first non-grooved roller and opposite a body; and providing an input to the motor drive, wherein the input causes the motor drive to so as to cause the pair of generally-parallel rollers to rotate so as to cause the needle to complete at least one revolution to form a single suture, wherein the motor drive transmits rotation to one roller via a drive coupling on a roller shaft.

22. The method of claim 21, further comprising selecting the suture cartridge from one of a plurality of differently-sized suture cartridges, wherein each of the plurality of suture cartridges supports a needle having a different helical radius, wherein each of the plurality of suture cartridges is configured to form a suture of a differing size.

23. The method of claim 22, further comprising coupling the motor drive with the selected suture cartridge.

* * * * *

UNITED STATES PATENT AND TRADEMARK OFFICE
CERTIFICATE OF CORRECTION

PATENT NO. : 12,396,722 B2
APPLICATION NO. : 17/215660
DATED : August 26, 2025
INVENTOR(S) : Adam Lee Smith Page 1 of 1

It is certified that error appears in the above-identified patent and that said Letters Patent is hereby corrected as shown below:

In the Claims

In Column 18, Line 30, in Claim 21, after "drive to", insert --rotate--

Signed and Sealed this
Seventh Day of October, 2025

John A. Squires
*Director of the United States Patent and Trademark Office*